US008735342B2

(12) United States Patent
Basile

(10) Patent No.: US 8,735,342 B2
(45) Date of Patent: May 27, 2014

(54) METHOD FOR TREATING BRAIN CANCER USING A NOVEL TUMOR SUPPRESSOR GENE AND SECRETED FACTOR

(75) Inventor: Lena A. Basile, Tujunga, CA (US)

(73) Assignee: Neumedicines, Inc., Pasadena, CA (US)

( * ) Notice: Subject to any disclaimer, the term of this patent is extended or adjusted under 35 U.S.C. 154(b) by 0 days.

(21) Appl. No.: 13/575,289

(22) PCT Filed: Jan. 27, 2011

(86) PCT No.: PCT/US2011/022776
§ 371 (c)(1),
(2), (4) Date: Sep. 4, 2012

(87) PCT Pub. No.: WO2011/094446
PCT Pub. Date: Aug. 4, 2011

(65) Prior Publication Data
US 2013/0012452 A1    Jan. 10, 2013

Related U.S. Application Data

(60) Provisional application No. 61/298,641, filed on Jan. 27, 2010.

(51) Int. Cl.
*A61K 38/00*    (2006.01)
*A61P 35/00*    (2006.01)
*A61K 38/16*    (2006.01)

(52) U.S. Cl.
CPC ............... *A61K 38/00* (2013.01); *A61K 38/16* (2013.01)
USPC ........................... 514/1.1; 514/19.3; 514/21.2

(58) Field of Classification Search
None
See application file for complete search history.

(56) References Cited

U.S. PATENT DOCUMENTS

| | | | |
|---|---|---|---|
| 2003/0105000 A1* | 6/2003 | Pero et al. ........................ 514/12 |
| 2007/0160985 A1 | 7/2007 | Gallaher et al. | |
| 2008/0075744 A1 | 3/2008 | Hiserodt et al. | |
| 2009/0036380 A1 | 2/2009 | Fainzilber et al. | |
| 2009/0318450 A1 | 12/2009 | Hangauer et al. | |

FOREIGN PATENT DOCUMENTS

WO    WO 2004/060867 A2    7/2004

OTHER PUBLICATIONS

Gura (Science, 1997, 278:1041-1042).*
Kaiser (Science, 2006, 313:1370).*
Krontiris and Capizzi (Internal Medicine, 4th Edition, Editor-in-chief Jay Stein, Elsevier Science, 1994 Chapters 71-72, pp. 699-729).*
Carter, S. K. et al. (Chemotherapy of Cancer; Second edition; John Wiley & Sons: New York, 1981; appendix C).*
Verma et al. (1997) Nature vol. 389:239-242.*
Eck et al. (Goodman & Gilman's The Pharmacological Basis of Therapeutics (1996), 9th Edition, Chapter 5, McGraw-W, NY.*
Ross et al. Human Gene Therapy, 1996, vol. 7, pp. 1781-1790.*
Rubanyi (Mol. Aspects Med. (2001) 22:113-142).*
Benedict et al (J. Exp. Medicine, 2001, 193(1) 89-99).*
Jiang et al (J. Biol. Chem., 2003, 278(7) 4763-4769).*
Matsushita et al (FEBS Letters, 1999, vol. 443, pp. 348-352).*
Hirashima (Int. Arch. Allergy Immunol., 2000, Suppl 1: 6-9).*
Bowie et al. (Science, 1990, 247:1306-1310).*
Skolnick et al. (TIBTECH 18:34-39, 2000).*
Ibragimova and Eade (Biophysical Journal, Oct. 1999, vol. 77, pp. 2191-2198).*
Scott et al (Nature Genetics, 1999, 21:440-443).*
Burgess et al (J. of Cell Biol. 111:2129-2138, 1990).*
Mehrad et al., "Chemokines as Mediators of Angiogenesis," *Thromb Haemost.*, vol. 97, pp. 755-762 (2007).
Junes-Gill, et al., "hHSS1: A Novel Secreted Factor and Suppressor of Glioma Growth located at Chromosome 19q13.33," *J. Neuroonicol.*, pp. 1-15 (2010).
International Search Report issued in related International Patent Application No. PCT/US2011/022776, completed Mar. 10, 2011.
Kuhlman et al., "Design of a novel globular protein fold with atomic-level accuracy," *Science*, vol. 302, pp. 1364-1368 (2003).
Law et al, "Molecular cytogenetic analysis of chromosomes 1 and 19 in glioma cell lines," *Cancer Genet Cytogenet.*, vol. 160, pp. 1-14 (2005).
Su et al, "Large-scale analysis of the human and mouse transcriptomes," *Proc Natl Acad Sci USA*, pp. 4465-4470 (2002).
Vogler et al., "Inhibition of clonogenic tumor growth: a novel function of Smac contributing to its antitumor activity," *Oncogene*, vol. 24, pp. 7190-7202 (2005).
Planque N., "Nuclear trafficking of secreted factors and cell surface receptors: new pathways to regulate cell proliferation and differentiation, and involvement in cancers," *Cell Commun Signal*, vol. 4, p. 7 (2006).
Lal et al., "A public database for gene expression in human cancers," *Cancer Res.*, vol. 5, pp. 5403-5407 (1999).
Boon et al., "An anatomy of normal and malignant gene expression," *Proc Natl Acad Sci USA*, vol. 99, pp. 11287-11292 (2002).
Rubio et al, "The putative glioma tumor suppressor gene on chromosome 19q maps between APOC2 and HRCI," *Cancer Res*, vol. 54, pp. 4760-4763 (1994).
Smith et al., "A transcript map of the chromosome 19q-arm glioma tumor suppressor region," *Genomics*, vol. 64(I), pp. 44-50 (2000).
Smith et al, "Mapping of the chromosome 19 q-arm glioma tumor suppressor gene using fluorescence in situ hybridization and novel microsatellite markers," *Genes Chromosom Cancer*, vol. 29:, pp. 16-25 (2000).
von Deimling et al., "Deletion mapping of chromosome 19 in human gliomas," *Int J Cancer*, vol. 57, No. 5, pp. 676-680 (1994).
Kalin et al., "Paracrine and autocrine mechanisms of apelin signaling govern embryonic and tumor angiogenesis," *Dev Biol*, vol. 505, pp. 599-614 (2007).

(Continued)

*Primary Examiner* — Peter J Reddig
(74) *Attorney, Agent, or Firm* — Foley & Lardner LLP

(57) ABSTRACT

The present invention is directed to methods of using HSS1 (Hematopoietic Signal peptide-containing Secreted 1), HSM1 (Hematopoietic Signal peptide-containing Membrane domain-containing 1), or a combination thereof in the treatment of various cancers, such as brain cancers.

9 Claims, 22 Drawing Sheets

(56) References Cited

OTHER PUBLICATIONS

Kuno et al, "The carboxyl-terminal half region of ADAMTS-1 suppresses both tumorigenicity and experimental tumor metastatic potential," *Biochem Biophys Res Commun.*, vol. 319, pp. 1327-1333 (2004).

Lee et al, "Variable inhibition of thrombospondin 1 against liver and lung metastases through differential activation of metalloproteinase ADAMTSI," *Cancer Res.*, vol. 70, pp. 948-956 (2010).

Smith et al., "Localization of common deletion regions on Ip and 19q in human gliomas and their association with histological subtype,". *Oncogene*, vol. 75, pp. 4144-4152 (1999).

Zhao et al., "Murine Hematopoietic Stem Cell characterization and Its Regulation in BM Transplantation," *Blood*, pp. 3016-3022 (2000).

Phillips et al, "Molecular subclasses of high-grade glioma predict prognosis, delineate a pattern of disease progression, and resemble stages in neurogenesis," *Cancer Cell*, vol. 9, No. 3, pp. 157-173 (2006).

Zhong et al., "Gene expression profile of murine long-term reconstituting vs. short-term reconstituting hematopoietic stem cells," *PNAS USA*, vol. 702, pp. 2448-2453 (2005).

Loberg et al., "CCL2 as an important mediator of prosta te cancer growth in vivo through the regulation of macrophage mfi.Hrat.ion," *Neoplasia*, vol. 9, pp. 556-562 (2007).

Johansson et al., "Microsomal glutathione transferase 1 in anticancer drag resistance," *Carcinogenesis*, vol. 25, pp. 465-470 (2007).

Mott et al., "Post-translational proteolytic processing of procollagen C~terminal proteinase enhancer releases a metal ioproteinase inhibitor," *J. Biol. Chem.*, vol. 7, No. 5(2), pp. 1384-1390 (2000).

Lai et al., "The tumor suppressor function of human sulfatase 1 (SULF1) in carcinogenesis," *J. Gastrointest. Cancer*, vol. 59(1-4), pp. 149-158 (2008).

Guilbault et al., "RasGRPI sensitizes an immature B cell line to antigen receptor-induced apoptosis," *J. Biol. Chem.*, vol. 279(19), pp. 19523-19530 (2004).

International Preliminary Report on Patentability issued in related International Patent Application No. PCT/US2011/022776, dated Aug. 9, 2012.

\* cited by examiner

Figure 5

```
              10         20         30         40         50         60
              |          |          |          |          |          |
hHSM1  MAAASAGATRLLLLLLMVAAAPSRARGSGCRAGTGARGAGAEGREGEACGTVGLLLEHSF
mHSM1  MVAAGAGVTRLLVLLLMVAAAPSRARGSGCRVGASARGTGADGREABGCGTVALLLEHSF
hHSS1  MAAASAGATRLLLLLLMVAAAPSRARGSGCRAGTGARGAGAEGREGEACGTVGLLLEHSF
mHSS1  MVAAGAGVTRLLVLLLMVAAAPSRAPGSGCRVGASARGTGADGREAEGCGTVALLLEHSF
       *.**.**.****.,*****.,*********.*;.***;***.*.****.*******

70         80         90        100        110        120
              |          |          |          |          |          |
hHSM1  EIDDSANFRKRGSLLWNQQDGTLSLSQRQLSEEERGRLRDVAALNGLYRVPIPREPGALD
mHSM1  ELGDGANFQKRGSLLLWNQQDGTLSATQRQLSEEERGRLRDVAAVNGLYRVPVPREPGTLD
hHSS1  EIDDSANFRKRGSLLWNQQDGTLSLSQRQLSEEERGRLRDVAALNGLYRVRIPREPGALD
mHSS1  ELGDGANFQKRGSLLLWNQQDGTLSATQRQLSEEERGRLRDVAAVNGLYRVRVPREPGTLD
       *;.*.***;***.********.;************;******;****.**

130        140        150        160        170        180
              |          |          |          |          |          |
hHSM1  GLEAGGYVSSFVPACSLVESHLSDQLTLHVDVAGNVVGVSVVTHPGGCRGHEVEDVDLEL
mHSM1  GSEAGGHVSSFVPACSLVESHLSDQLTLHVDVAGNVVGLSVVVYPGGCRGSEVEDEDLEL
hHSS1  GLEAGGYVSSFVPACSLVESHLSDQLTLHVDVAGNVVGVSVVTHPGGCEGHEVEDVDLEL
mHSS1  GSEAGGHVSSFVPACSLVESHLSDQLTLHVDVAGNVVGLSVVVYPGGCRGSEVEDEDLEL
       * ****.*********************************;***,;******.**** ****

190        200        210        220        230        240
              |          |          |          |          |          |
hHSM1  FNTSVQLQPPTTAPGPETAAFIERLEMEQAQKAKNPQEQKSPPAKYWNYIIP-VVLFLMM
mHSM1  FNTSVQLRPPSTAPGPETAAFIERLEMEQAQKAKNPQEQKSPPAKYWNYIIP-VVLFLMM
hHSS1  FNTSVQLQPPTTAPGPETAAFIERLEMEQAQKAKNPQEQKSPPAKYWHITLGGAVLLTAL
mHSS1  FNTSVQLRPPSTAPGPETAAFIERLEMEQAQKAKNPQEQKSPPAKYWHLILGGAVLLTAL
       *******;**;**************************************  *;.**;;

250        260
              |          |
hHSM1  SGAPDAGQGGGGGGGGGGGSGF
mHSM1  SGAPDAGQGGGGGGGGSSR----
hHSS1  R--PAIPGPAPPPQEA-------
mHSS1  R--PAAPGPAPAPTEA-------
```

METHOD FOR TREATING BRAIN CANCER USING A NOVEL TUMOR SUPPRESSOR GENE AND SECRETED FACTOR

CROSS-REFERENCE TO RELATED APPLICATION

This application claims priority of U.S. Provisional Application No. 61/298,641, filed on Jan. 27, 2010.

SEQUENCE LISTING

The instant application contains a Sequence Listing which has been submitted in ASCII format via EFS-Web and is hereby incorporated by reference in its entirety. Said ASCII copy, created on Feb. 14, 2011, is named 97157131.txt and is 10,200 bytes in size.

BACKGROUND OF THE INVENTION

Tumor suppressor genes and their associated proteins have been identified in the scientific literature. However, to date, no identified tumor suppressors have been utilized in the treatment of cancer.

It would appear that certain tumor suppressor proteins could be utilized in the treatment of cancer, either as a direct therapy or as an adjuvant therapy along with standard treatment regimens, where the standard therapies would encompass radiation, chemotherapy or more targeted therapies, such as tumor associated antigen-antibody therapy.

Ideally, secreted tumor suppressors proteins or factors could be utilized in cancer treatment regimens as these secreted proteins would be amenable to various drug delivery mechanisms. However, very few identified tumor suppressor genes exist as secreted factors in the human circulatory system.

If novel, secreted tumor suppressor proteins were discovered, these proteins could be useful in the development of various cancer treatment regimens. Thus, the discovery and application of such tumor suppressor proteins could advance current medical treatment for cancers that have the capacity to be acted upon, i.e., suppressed, by secreted tumor suppressor proteins.

SUMMARY OF THE INVENTION

The present invention is directed to methods of using HSS1 (Hematopoietic Signal peptide-containing Secreted 1), HSM1 (Hematopoietic Signal peptide-containing Membrane domain-containing 1), or a combination thereof in the treatment of various cancers, such as brain cancers. The brain cancer can be a primary or secondary brain cancer. The preferred brain cancer treatable with embodiments of the present invention is glioma, particularly glioblastoma multiforme. Other brain cancers are also treatable with the present invention, including but not limited to astrocytoma, oligodendroglioma, ependymoma, meningiomas, acoustic neuroma/schwannomas, and medulloblastoma. Also included as treatable by the present invention is neuroblastoma.

In one embodiment of the invention, the brain cancer to be treated with a method of the invention is a secondary brain cancer which has metastasized from a non-brain cancer.

Any pharmaceutically acceptable delivery method now known or developed in the future can be utilized in the methods of the invention to deliver HSS1 to the site of the brain cancer, either locally or systemically. Further, any methods now known or developed in the future that facilitate passage across the blood brain barrier can be utilized in the methods of the invention to deliver HSS1 to the site of the brain cancer. Other delivery methods included in the present invention are delivery via liposomes and fusion proteins. HSS1 can be formulated as a pharmaceutical for systemic delivery or for delivery to the brain by intracerebroventricular infusion, or any other like delivery method. Another form of delivery method is via various gene therapy vector delivery systems available in the art or to be discovered in the future. Other embodiments of the present invention include co-delivery of HSS1 and HSM1, a related membrane bound counterpart to HSS1, via a gene therapy delivery method, or delivery of HSM1 alone. In one embodiment of the invention, the gene therapy vector is derived from adenovirus. In another embodiment of the invention, the gene therapy vector is derived from the herpes virus. In still another embodiment of the invention, the gene therapy vector is derived from a retrovirus.

In yet another embodiment of the invention, HSM1 is also delivered via a gene therapy approach along with HSS1.

In one embodiment of the invention, HSS1 is delivered before or after radiation therapy. In another embodiment, HSS1 is delivered before or after brain surgery to remove all or part of the cancerous tissue. In yet another embodiment, HSS1 is delivered before or after chemotherapy. The embodiments of the invention can be combined.

In one embodiment of the invention, HSM1 is delivered before or after radiation therapy. In another embodiment, HSM1 is delivered before or after brain surgery to remove all or part of the cancerous tissue. In yet another embodiment, HSM1 is delivered before or after chemotherapy. The embodiments of the invention can be combined.

In one embodiment of the invention, a combination of HSS1 and HSM1 is delivered before or after radiation therapy. In another embodiment, a combination of HSS1 and HSM1 is delivered before or after brain surgery to remove all or part of the cancerous tissue. In yet another embodiment, a combination of HSS1 and HSM1 is delivered before or after chemotherapy. The embodiments of the invention can be combined.

The embodiments of the present invention also include the use of HSS1 alone, HSS1 and HSM1 or HSM1 alone along with conventional cancer therapies used now or later discovered. Included in the definition of "conventional therapies" are all forms of radiation therapy and all forms of chemotherapies, which can be used in conjunction with various forms of radiation therapy. These conventional therapies also include surgery along with any combination of radiation and chemotherapy.

The dose of HSS1 and/or HSM1 used in the present invention is the dose required to be efficacious as well as safe, regardless of how HSS1 and/or HSM1 is/are delivered.

The use of the various embodiments of the present invention can increase the survival of patients diagnosed with brain cancer. Other benefits include a reduction in tumor mass and possible more complete remission of the brain cancer.

Also encompassed are pharmaceutical compositions useful in the methods of the invention. The compositions comprise HSS1, HSM1, or a combination thereof. The compositions can additionally comprise one or more (e.g., at least one) pharmaceutically acceptable carrier.

In another embodiment of the invention, encompassed are pharmaceutical compositions useful in the methods of the invention. The compositions comprise a peptide having at least about 80% homology to HSS1, a peptide having at least about 80% homology to HSM1, or any combination thereof. In addition, the invention encompasses compositions comprising at least one, or one or more, HSS1 fragments, HSM1 fragments, or a combination of at least one (or one or more) HSS1 fragment and at least one (or one or more) HSM1 fragment. Thus, in the invention encompasses pharmaceutical compositions comprising a therapeutically effective amount of HSS1, HSM1, at least one (or one or more) HSS1 fragment, at least one (or one or more) HSM1 fragment, a peptide having at least about 80% homology to HSS1 (or a homology as defined herein), a peptide having at least about 80% homology to HSM1 (or a homology as defined herein), or any combination thereof.

The foregoing general description and following description of the drawings and detailed description are exemplary and explanatory and are intended to provide further explanation of the invention as claimed. Other objects, advantages, and novel features will be readily apparent to those skilled in the art from the following detailed description of the invention.

DESCRIPTION OF THE DRAWINGS

FIG. 5: Shows the protein sequence alignment for HSS1 and HSM1. Homology between the two splice variants in mouse and human are shown. Identical residues are indicated by asterisks. Shaded regions represent as follows: predicted signal peptide (light gray); predicted N- and O-glycosylation sites at the amino acid positions 182 and 198 (bold, not underlined); predicted transmembranc domain for hHSM1 (dark gray, note it contains the ultimate intron-exon splice boundary which gives rise to the different forms of the gene); intron-exon junctions (bold underlined). FIG. 5 discloses SEQ ID NOS 4-7, respectively, in order of appearance.

DETAILED DESCRIPTION OF THE INVENTION

The present invention is directed to methods of treating brain cancers using a novel gene and protein, namely HSS1. The preferred embodiment is a method of using HSS1 in the treatment of glioma. HSS1 has been described previously in WIPO publication No. WO 2004/060867 A2, which is incorporated by reference in its entirety.

As used herein, "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

A. Hematopoietic Signal Peptide-Containing Secreted 1

The completion of the Human Genome Project resulted in discovery of many unknown novel genes. This feat paved the way for the future development of novel therapeutics for the treatment of human disease based on novel biological functions and pathways. Towards this aim, the inventors undertook a bioinformatics analysis of in-house microarray data derived from purified hematopoietic stem cell populations. This effort led to the discovery of HSS1 (Hematopoietic Signal peptide-containing Secreted 1) and its splice variant HSM1 (Hematopoietic Signal peptide-containing Membrane domain-containing 1). Junes-Gill et al., "hHSS1: a novel secreted factor and suppressor of glioma growth located at chromosome 19q13.33," *J. Neurooncol.* (Jul. 31, 2010). HSS1 gene is evolutionarily conserved across species, phyla and even kingdoms, including mammals, invertebrates and plants. Structural analysis showed no homology between HSS1 and known proteins or known protein domains, indicating that it was a truly novel protein.

The human HSS1 (hHSS1) gene is located at chromosome 19q13.33, a genomic region implicated in various cancers, including malignant glioma. Stable expression of hHSS1 in glioma-derived A172 and U87 cell lines greatly reduced their proliferation rates compared to mock-transfected cells. hHSS1 expression significantly affected the malignant phenotype of U87 cells both in vitro and in vivo. Further, preliminary immunohistochemical analysis revealed an increase in hHSS1/HSM1 immunoreactivity in two out of four high-grade astrocytomas (glioblastoma multiforme, WHO IV) as compared to low expression in all four low-grade diffuse astrocytomas (WHO grade II). High-expression of hHSS1 in high-grade gliomas was further supported by microarray data, which indicated that mesenchymal subclass gliomas exclusively up-regulated hHSS1. The data reveal that HSS1 is a truly novel protein defining a new class of secreted factors, and that it may have an important role in cancer, particularly glioma.

Figure 6:
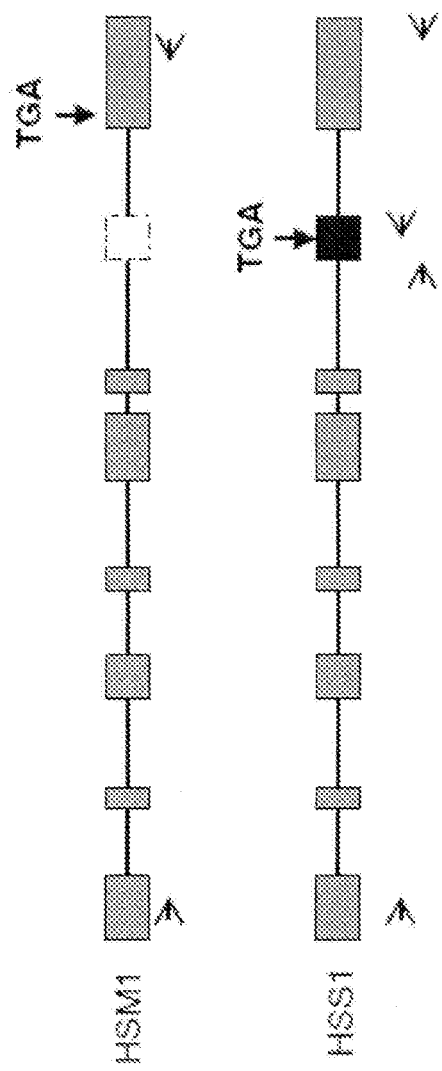
FIG. 6: Shows the intron-exon arrangement of hHSS1/HSM1. Both HSM1 and HSS1 contain seven exons. The last exon differs in both forms of the protein. Small arrows indicate PCR primer sites. TGA; stop codon. The two forms of the gene are encoded at locus 19q13.33.

The full-length cDNA sequence of HSS1 consists of approximately 1.9 kb containing an open reading frame of 789 bp. This sequence was submitted to the NCBI database and assigned a GenBank accession number, namely AY761095. The gene structure of HSS1, as well as HSM1, is composed of seven exons and six introns covering a minimum of 6.8 kb (FIG. 6). The last exon is alternatively spliced resulting in either HSS1 or HSM1. The two forms of the gene are encoded at chromosome 19q13.33. Mouse and human HSS1/HSM1 share homology with ortholog genes in numerous species. The Beijing Genomics Institute Tree Families Database, for example, includes 45 different species to date as part of the family (TF314052). Thus, the gene is evolutionarily conserved across species, phyla, and kingdoms, including mammals, invertebrates, and plants.

HSS1 and HSM1 do not have sequence homology to known naturally occurring proteins. Since HSS1 was identified solely by bioinformatic analysis, and HSM1 was only one gene out of thousands of uncharacterized genes which had been sequenced in various EST or transcriptomic projects, no function could be attributed a priori to these genes. Towards the aim of elucidating a function for the proteins encoded by the HSS1 gene, the inventors searched extensively for homology between HSS1/HSM1 and proteins with known functions. The inventors also performed searches to ascertain whether HSS1/HSM1 contained domains common to a known protein and/or protein domain family. Using publicly available algorithms to identify protein domains and overall structure, the inventors failed to find any homology with HSS1 or HSM1.

The inventors then used a proprietary algorithm (Eidogen-Sertanty Inc., Oceanside, Calif., USA) based on a 3-D, crystallographic protein database to align protein sequences of unknown structure. Interestingly, this search revealed homology to only one protein in the database. This protein was a non-natural, computationally designed protein designated as TOP7. Kuhlman et al., "Design of a novel globular protein fold with atomic-level accuracy," *Science*, 302:1364-1368 (2003).

Figure 7:
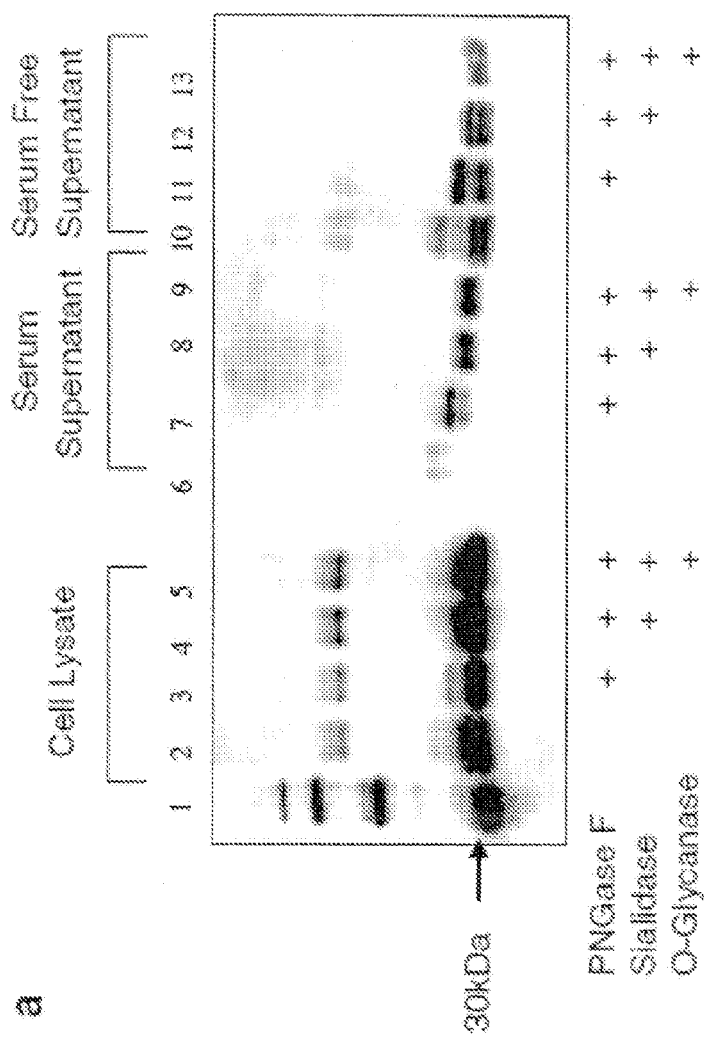
FIG. 7: Shows that HSS1 is secreted. A Western blot analysis was obtained from 293T cells transfected with the pTT3-hHSS1 construct in serum and serum-free medium. The protein was detected with anti-His-tag antibody. Samples were also digested with enzymes that selectively cleave glycosylated proteins. His Tag ladder (lane 1); denatured cell lysate (lane 2); cell lysate treated with different enzymes (lanes 3, 4 and 5); denatured supernatant from cells grown in medium with serum (lane 6); supernatant with serum treated with different enzymes (lanes 7, 8 and 9); denatured supernatant from cells grown in serum-free medium (lane 10); and supernatant serum-free treated with different enzymes (lanes 11, 12 and 13).
Figure 8:
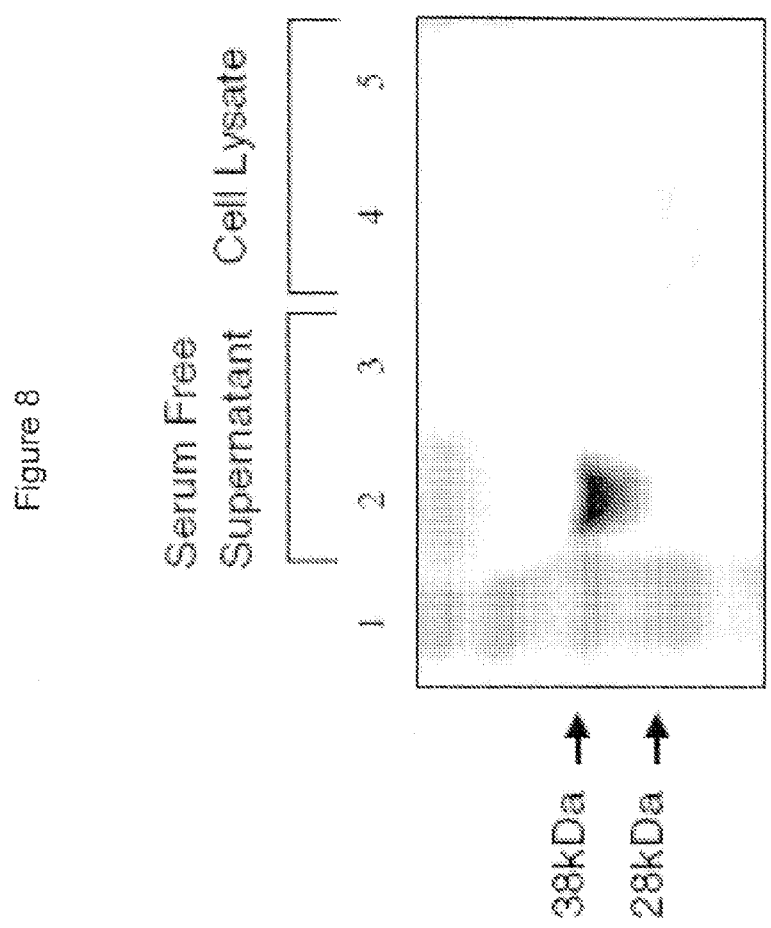
FIG. 8: Shows that HSS1 is multi-glycosylated. A Western blot analysis from 293T cell. Serum free supernatant and cell lysate of 293T cells transiently transfected with hHSS1 (lanes 2 and 4, respectively). Serum free supernatant and cell lysate of wild type 293T cells (lanes 3 and 5, respectively).
Figure 9:
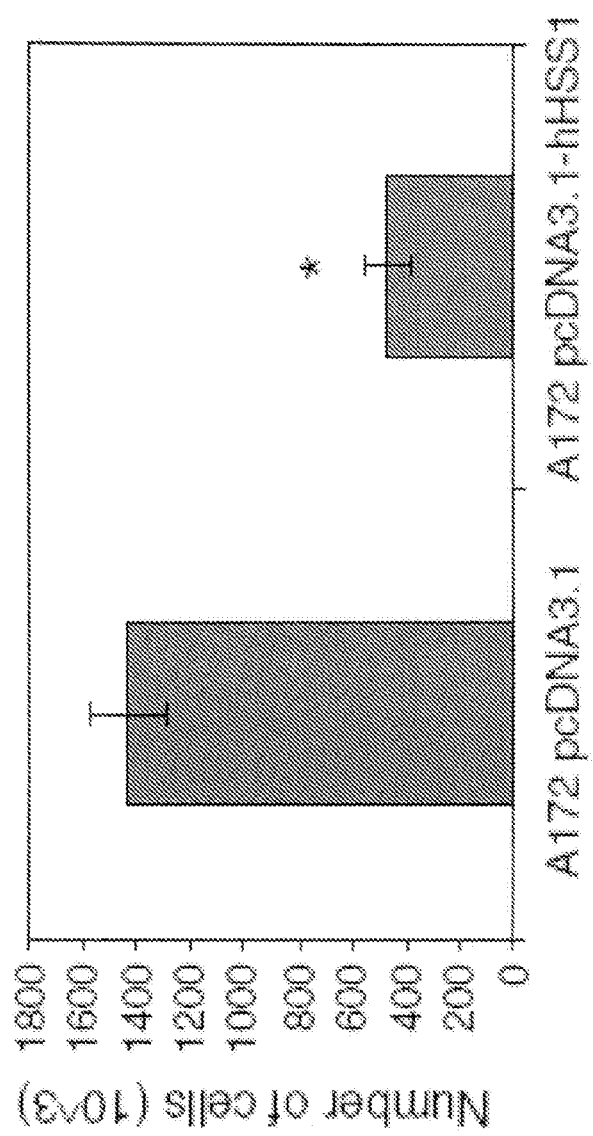
FIG. 9: Shows A172 pcDNA3.1 and pcDNA3.1-hHSS1 transfected cells which were seeded ($8 \times 10^4$ cells) and harvested after 7 days for cell counting by trypan blue exclusion.
Figure 10:
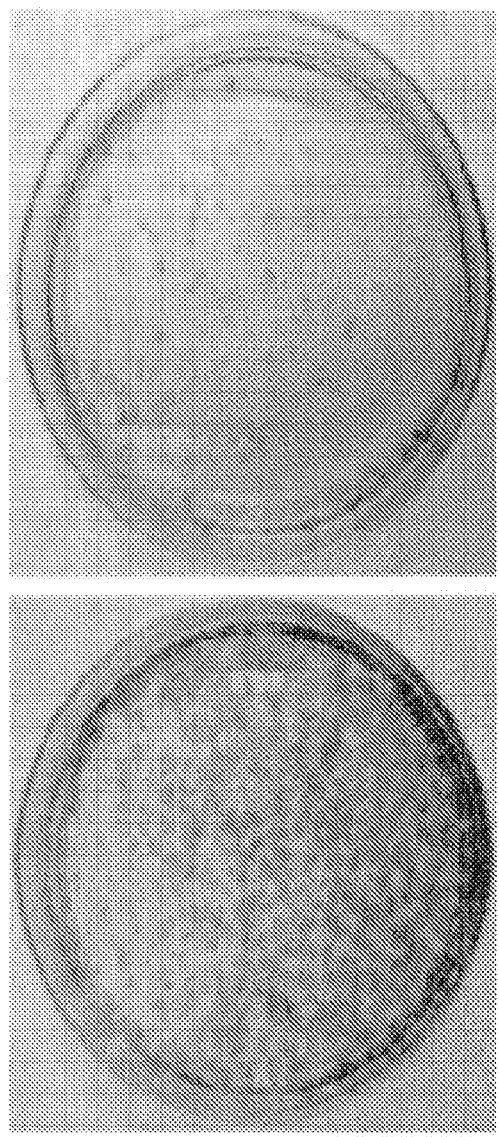
FIG. 10: Shows hHSS1 expression suppresses colony formation in A172. A172 pcDNA3.1 and pcDNA3.1-hHSS1 transfected cells were seeded ($2 \times 10^3$ cells), and after 23 days cells were stained with neutral red.
Figure 11:
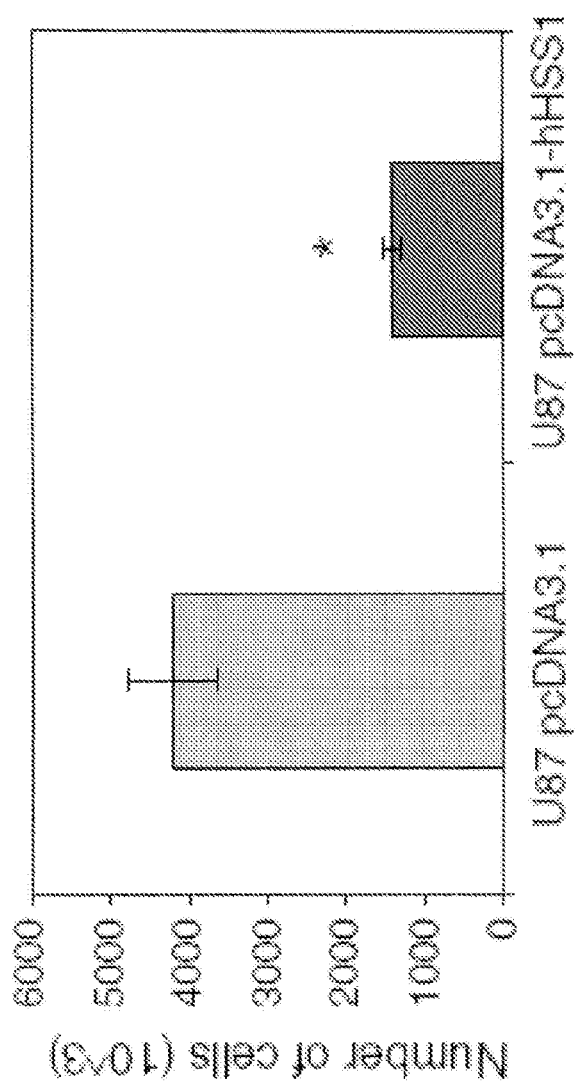
FIG. 11: Shows U87 pcDNA3.1 and pcDNA3.1-hHSS1 transfected cells were seeded ($8 \times 10^4$ cells) and harvested after 6 days for cell counting by trypan blue exclusion.

HSS1 is a novel secreted protein with a complex glycosylation pattern. Based on the primary sequence of HSS1, SignalP analysis showed that HSS1 has a predicted signal peptide, but according to TMHMM no transmembrane domain. To further confirm its potential secretory properties, hHSS1 was expressed in 293T cells as a construct containing a 6×His tag at its carboxyl terminal. Western blot analysis using an anti-6×His antibody confirmed that HSS1 is a secreted protein, as it was detected in the supernatant of transiently transfected 293T cells. (FIGS. 7 and 8.) Wild type 293T cells (FIG. 8) and the cells transfected with empty vector yielded no protein via Western blot analysis.

Figure 1:
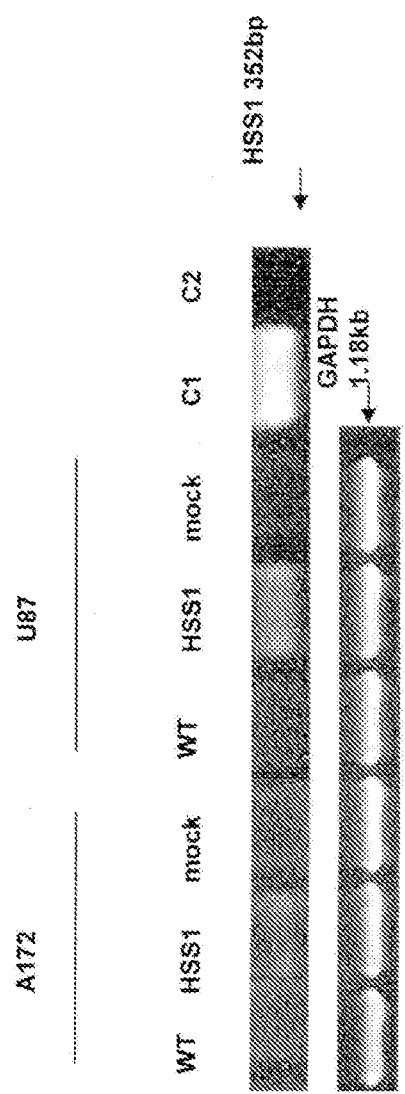
FIG. 1: Shows growth inhibitory effect of hHSS1 in glioma cells. RT-PCR analysis of the clonal cells stably transfected with pcDNA3.1-hHSS1 or pcDNA3.1 empty vector selected for the experiments. A172 and U87 ell lines (lanes 1 and 4, upper panel) do not express detectable levels of hHSS1 (or hHSM1) but a PCR product corresponding to basepairs 38-386 of the HSS1 gene yielding a 352 bp fragment of HSS1 mRNA can clearly be seen in the clones from each cell line that were transfected with the HSS1 cDNA (lanes 2 and 5) and mock-transfected cells (lanes 3 and 6); C1, corresponds to the positive control, which has 100 ng of pcDNA3.1-hHSS1 vector; C2, is a negative control: reaction reagent only.
Figure 2:
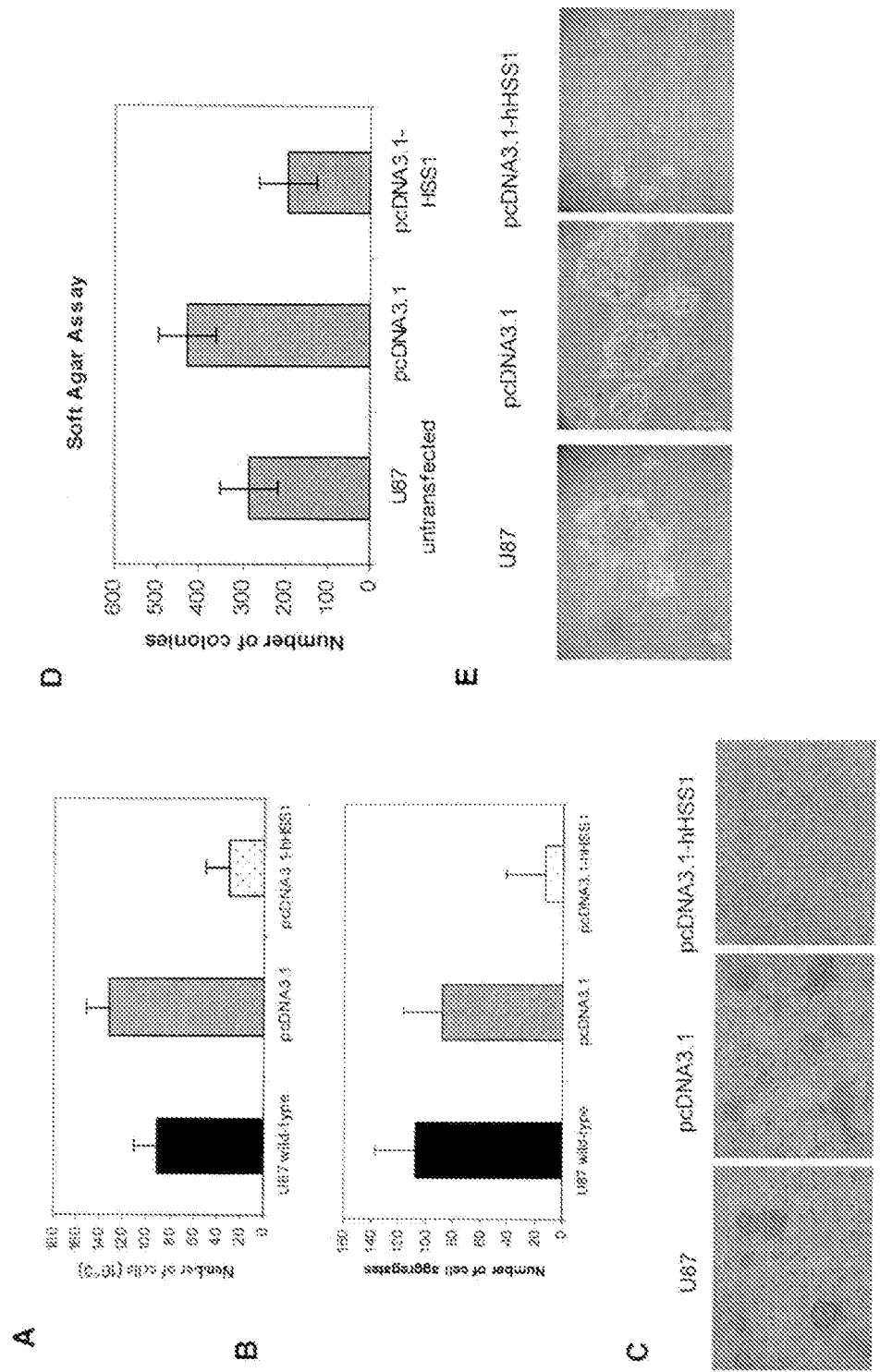
FIG. 2: HSS1 effectively inhibits growth of U-87 cell lines. A) 2,640 cells were seeded in septuplicates in 96-well plates, after 9 days cell aggregates, which appear as large, dark spots in the U87 and pcDNA3.1 cells, were photographed and counted. After harvest, the number of cells were also counted by trypan blue exclusion. B and C) $5 \times 10^3$ cells were seeded and the number of cell aggregates was counted after 4 days; D and E) Anchorage-independent growth of U87 cells on soft agar. Cells were seeded in 10 cm plates and the number of colonies formed in soft agar was counted after 23 days of incubation. Pictures show non-transfected cells, cells transfected with pcDNA3.1 empty vector or pcDNA3.1-hHSS1.
Figure 3:
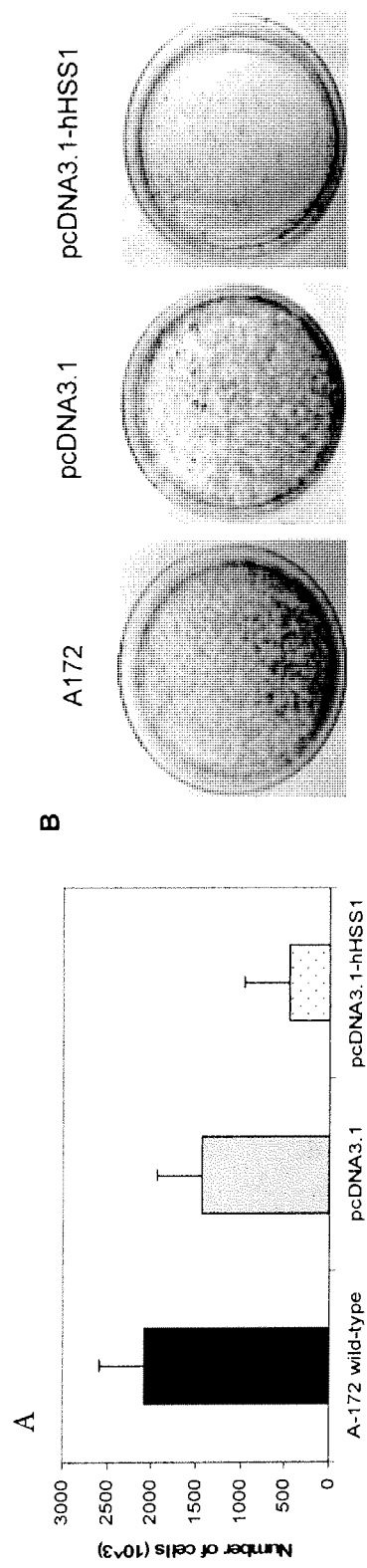
FIG. 3: HSS1 inhibits growth of A-172 cell lines. A) A172 cells ($8 \times 10^4$) were seeded in triplicates in 10 cm plates, after 7 days cells were harvested and the number of cells was determined by trypan blue exclusion. B) Cells were ($1 \times 10^3$) seeded in triplicates in 10 cm plates, after 11 days cells were stained with 0.001% neutral red.

The inventors then confirmed whether HSS1 was glycosylated, as the predicted sequence presented two possible glycosylation sites at residues 182 and 198 (FIG. 5) based on NetNGlyc and NetOGlyc analysis. Thus, cleavage of HSS1 by glycolytic enzymes was performed on the cell lysate and supernatants containing HSS1. The apparent molecular weight of unglycosylated HSS1 from analysis of the His tag ladder (FIG. 7, lane 1) is approximately 30 kDa (FIG. 7, lanes 2-5). The theoretical molecular weight of the mature (i.e., signal peptide cleaved) HSS1 is 24,171 Da. The majority of the protein in the cell lysate did not appear to be glycosylated as enzyme cleavage did not significantly change the apparent molecular weight. However, for HSS1 that is secreted and found in the supernatant, cleavage by various glycolytic enzymes incrementally decreased the apparent molecular weight of the protein (FIG. 7, lanes 6-13), thus suggesting a complex glycosylation pattern.

hHSS1 has a growth inhibitory effect in glioma cells. Following the initial characterization of the physical properties of HSS1, the inventors next sought to determine a function for this novel protein. Since Mitelman Breakpoint Data revealed that hHSS1 is located in a chromosomal region known to have aberrations or deletions in a variety of cancers, including various gliomas (Mitelman et al., (eds) (2009) Mitelman database of chromosome aberrations in cancer. http://cgap.nci.nih.gov/Chromosomes/Mitelman), the inventors first investigated whether hHSS1 would affect the malignant proprieties of two well-studied human glioma-derived cell lines, namely A172 and U87. These glioblastoma cell lines were chosen for study because previously they were found to have deletions in a region corresponding to the gene locus of hHSS1 at 19q13.33 (Law et al., "Molecular cytogenetic analysis of chromosomes 1 and 19 in glioma cell lines," *Cancer Genet Cytogenet.*, 160:1-14 (2005)). However, because hHSS1 is expressed in normal brain tissues (Su et al., "Large-scale analysis of the human and mouse transcriptomes," *Proc Natl Acad Sci USA*, 99:4465-4470 (2002)), the inventors checked whether these cell lines were expressing hHSS1 by using gene specific primers in a one-step RT-PCR reaction. It was found that neither hHSS1 nor hHSM1 mRNA was detectable in these glioblastoma cell lines (FIG. 1, lanes 1 and 4).

Next, A172 and U87 were stably transfected with a construct carrying hHSS1 cDNA (pcDNA3.1-hHSS1) or with the empty vector as control. The expression of hHSS1 following transfection was confirmed by using RT-PCR. The results showed that while hHSS1 mRNA was not detectable in non-transfected wild-type and mock-transfected cells, the selected pcDNA3.1-hHSS1-transfected clones stably expressed the hHSS1 mRNA (FIG. 1, lanes 2 and 5).

During the selection of the stable clones, it was observed that the growth of the pcDNA3.1-hHSS1 transfected cells was dramatically decreased relative to mock-transfected clones. Thus, cell counting and plating efficiency were performed to evaluate the relative proliferation of clones transfected with pcDNA3.1-hHSS1 or empty vector. The results obtained showed that A172- and U87-hHSS1-expressing glioblastoma cells decreased in cell number by 3-fold compared to mock-transfected cells (two-tailed independent Student's t-test, P\0.001) (FIGS. 1, 2, 3, and 9-13).

Figure 12:
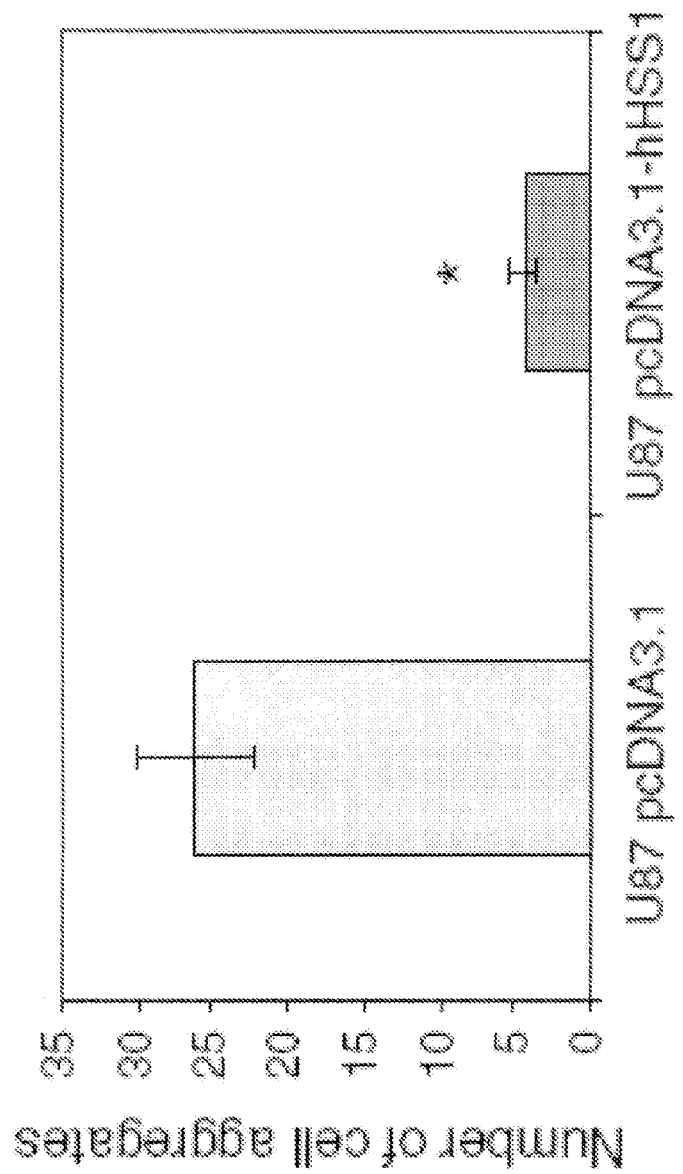
FIG. 12: Shows that hHSS1 expression decreases U87 cell aggregation in culture. U87 cells ($5 \times 10^3$) were seeded in septuplicate in 96-well plates and incubated for 3 days, and then cell aggregates were photographed and counted.
Figure 13:
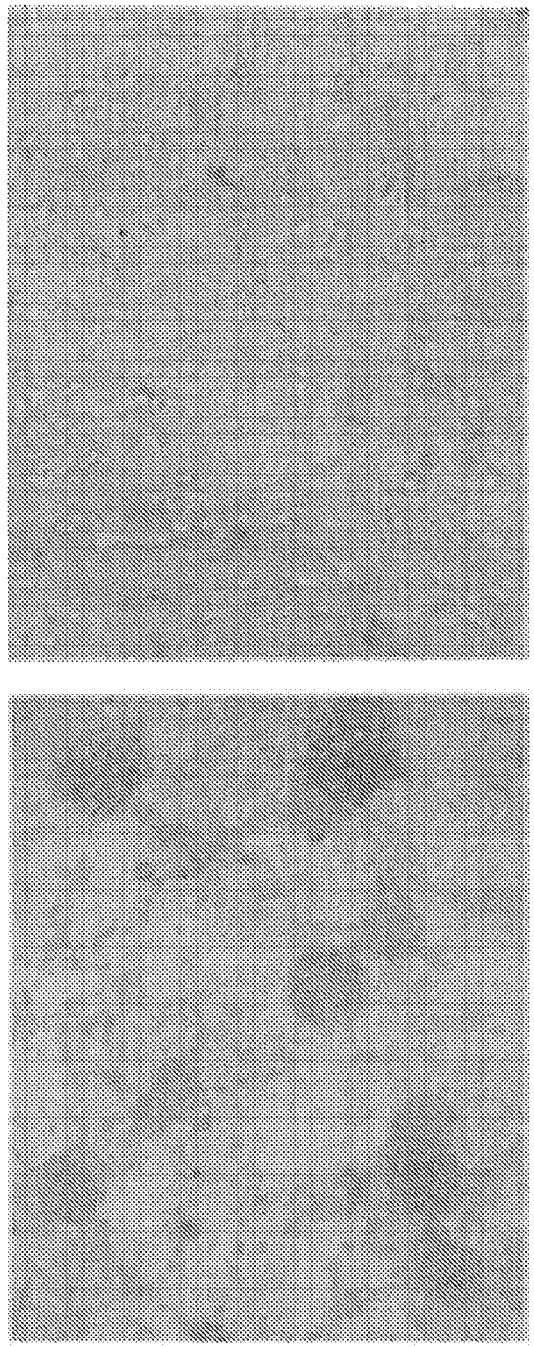
FIG. 13: Shows that hHSS1 expression decreases U87 cell aggregation in culture. hHSS1-expressing cells presented a much flatter shape while the control cells typically grew in cell aggregates.

In addition to reduction in proliferation, expression of the hHSS1 gene in U87 cells induced morphological changes. It was observed that cell aggregate formation in U87-mock transfected cells were discernible (FIG. 13), probably reflecting loss of contact inhibition in these cells. Cell aggregates can be viewed as clumps of cells that accumulate over an initial monolayer. This phenotype in U87 cells was also reported in a previous study of the Smac gene and its regulation of tumor cell viability. Vogler et al., "Inhibition of clonogenic tumor growth: a novel function of Smac contributing to its antitumor activity," *Oncogene*, 24:7190-7202 (2005). Next, the number of cell aggregates formed between hHSS1-expressing cells and mock-transfected cells were evaluated. The number of cell aggregates formed in U87 cells expressing hHSS1 was 5.9 times less relative to mock-transfected cells (two-tailed independent Student's t-test, P\0.001) (FIG. 12). The number of cells counted in this experiment was $1.32 \times 10^5$ (pcDNA3.1) and $3.35 \times 10^4$ (pcDNA3.1-hHSS1) (two-tailed independent Student's t-test, P\0.02).

Since A172 cells do not display cell aggregate formation, the difference in plating efficiency for this cell line as an additional measure of proliferation and ability to grow at low density were assessed. It was observed that the number of colonies formed by A172 cells expressing hHSS1 was dramatically decreased compared to the mocktransfected (FIG. 10, indicating that hHSS1 expression efficiently reduced clonogenic cell survival.

Since the expression of hHSS1 in these cell lines was only verified by mRNA levels, the expression of hHSS1 at the protein level by immunochemical analysis was then checked. No obvious staining was detectable in non-transfected and empty-vector transfected U87 cells. Immunoreactivity was evident throughout the cells overexpressing hHSS1, confirming that its transcript in U87 and A172 stable cells was translated into immocytochemically detectable hHSS1 protein. Conversely, endogenous hHSS1 expression in some cells was detected in both non-transfected and emptyvector transfected A172 cells. However, the A172 hHSS1-transfected cells expressed higher levels of hHSS1 protein compared to the controls. Nuclear staining was observed in A172 cells, suggesting that hHSS1 may also localize inside the nucleus of these cells. Thus, hHSS1 could have both intra and extracellular properties as has been reported for FGFs and epidermal growth factor (EGF) proteins. Planque N., "Nuclear trafficking of secreted factors and cell surface receptors: new pathways to regulate cell proliferation and differentiation, and involvement in cancers," *Cell Commun Signal*, 4:7 (2006).

Figure 14:
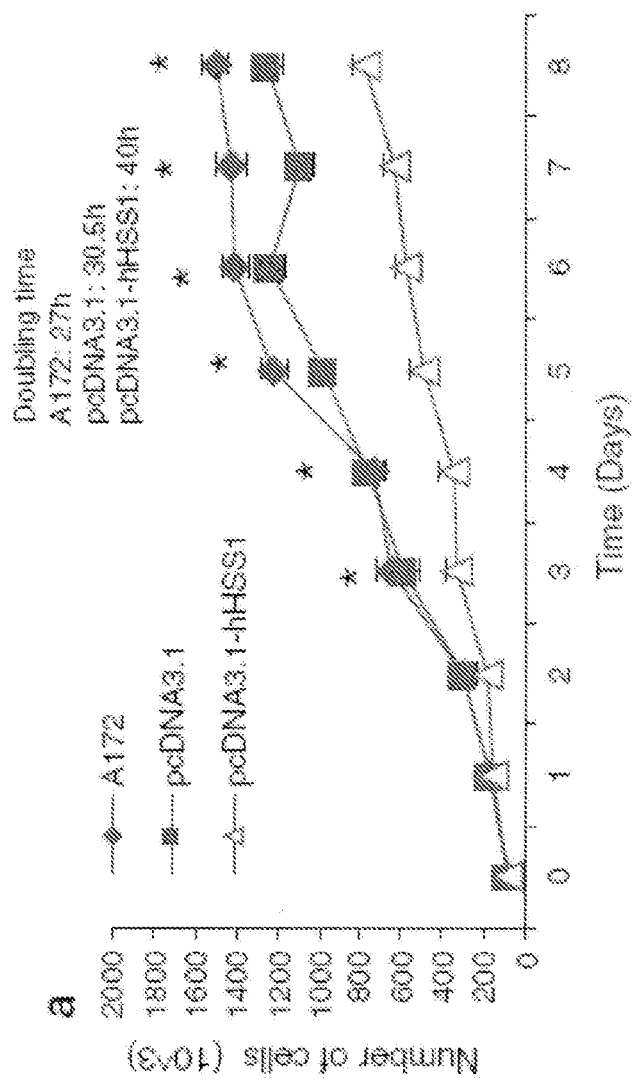
FIG. 14: Shows that hHSS1 expression inhibits A172 cell doubling. A172 cells (wild-type, pcDNA3.1, pcDNA3.1-hHSS1) were cultured at nine different time points, harvested and counted by trypan blue exclusion. hHSS1 significantly inhibited the proliferation of A172 cells after 3 days in culture.
Figure 15:
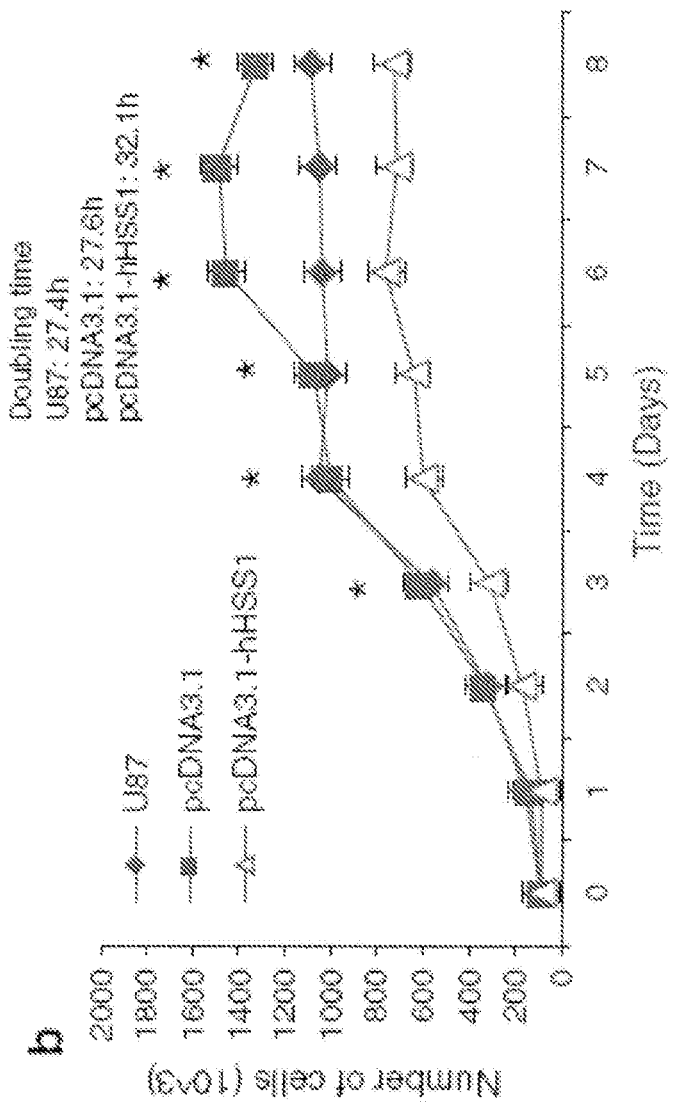
FIG. 15: Shows that hHSS1 expression inhibits U87 cell doubling. U87 cells (wild-type, pcDNA3.1, pcDNA3.1-hHSS1) were cultured at nine different time points, harvested and counted by trypan blue exclusion. hHSS1 significantly inhibited the proliferation of U87 cells after 3 days in culture.
Figure 16:
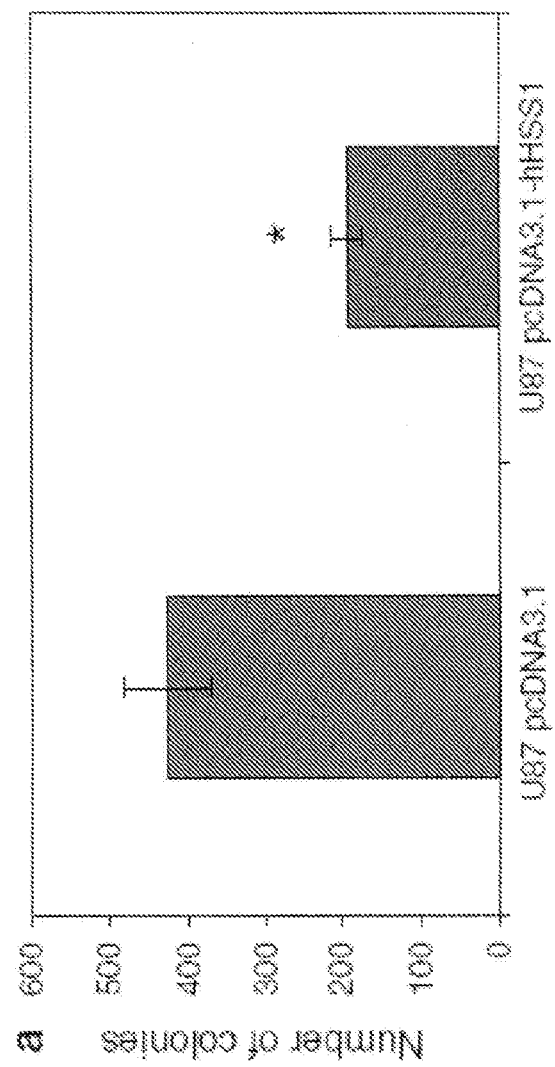
FIG. 16: Shows that hHSS1 suppresses anchorage-independent growth and tumorigenicity of U87 cells. U87 cells (pcDNA3.1, pcDNA3.1-hHSS1) were seeded on top of soft agar in 10 cm plates and the number of colonies formed in soft agar were counted after 23 days of incubation. Results are expressed as grand mean±SEM and are representative of two independent experiments. *P<0.05, Student's t-test, pcDNA3.1-hHSS1 versus U87 wild-type or versus mock-transfected cells.
Figure 17:
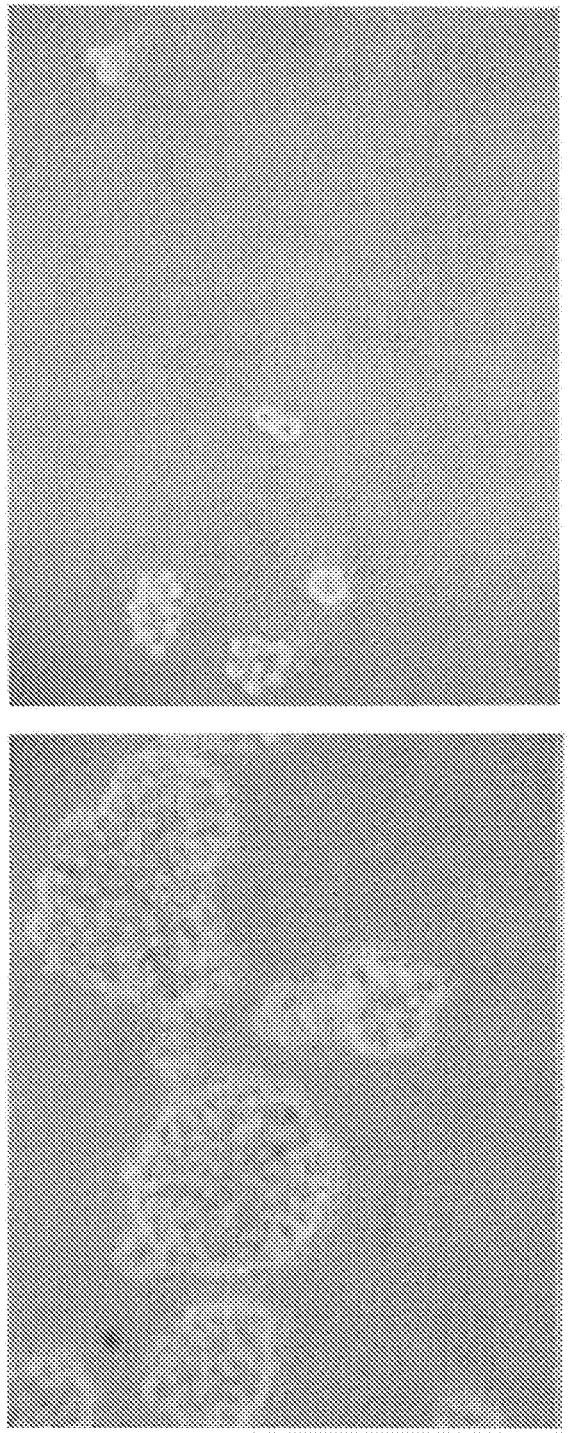
FIG. 17: Shows that hHSS1 suppresses anchorage-independent growth and tumorigenicity of U87 cells. Micrograph of U87 colonies grown in soft agar: pcDNA3.1: mock-transfected cells, pcDNA3.1-hHSS1: cells stably expressing hHSS1.

To further examine the growth properties of the hHSS1-expressing cells, a growth curve was constructed for each cell line to determine whether hHSS1 overexpression increased the cell doubling time. The growth rate was significantly affected by hHSS1 overexpression in both A172 cells [main effect of cell type, $F(2, 135)=98.61$, $P<0.001$] and U87 cells [main effect of cell type, $F(2, 135)=51.36$, $P<0.001$]. A significant growth inhibition effect was observed after day 3 of experiment for both cell lines: A172 cells [cell type X day interaction, $F(16, 135)=6.84$, $P<0.001$], U87 cells [cell type X day interaction, $F(16, 135)=3.45$, $P<0.001$]. Moreover, the A172 wild-type and mock-transfected cells showed a doubling time of 27 and 30.5 h, respectively, whereas the A172 hHSS1-expressing cells showed a doubling time of 40 h (FIG. 14). Similarly, while U87 wild-type and mocktransfected cells had a doubling time of 27.4 and 27.6 h, respectively, the U87 hHSS1-expressing cells had a doubling time of 32.1 h (FIG. 15). Taken together, these results indicate that hHSS1, a novel secreted protein in a new protein class, has a growth-inhibitory effect in malignant glioma cells.

hHSS1 suppresses the malignant phenotype of U87 cells in vitro and in vivo. Changes in cell morphology are associated with malignant transformation in many epithelial tumor cells. Furthermore, malignantly transformed cells have the ability to grow in the absence of cell anchorage. To evaluate whether the morphological changes induced by hHSS1 expression (FIG. 13) correlate with reduced malignancy in these cells, the ability of U87 cells carrying either the empty vector or expressing hHSS1 to grow in an anchorage-independent Manner was compared. Results showed that empty vector control cells formed numerous colonies in soft agar compared to hHSS1-expressing cells (FIG. 16). Moreover, the sizes of the colonies of empty vector control cells were markedly larger than those of cells expressing hHSS1 (FIG. 17). These results suggest that stable expression of hHSS1 in U87 cells in which hHSS1 expression previously had been undetected produces a potentially less malignant phenotype by restoring the normal cell property of contact inhibition.

Figure 4:
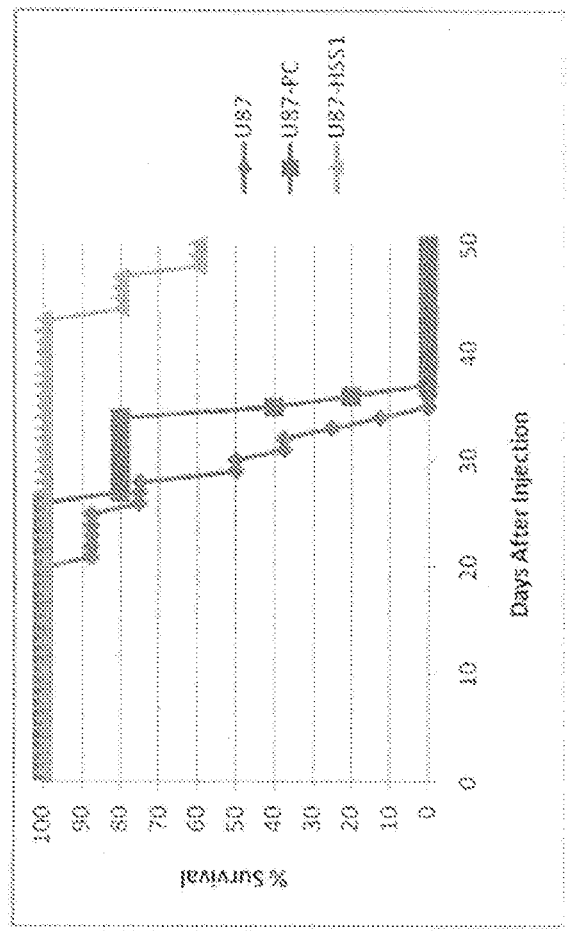
FIG. 4: HSS1 increases survival of mice injected intracranially with HTB glioma cells. Three groups of mice were injected intracranially with $1 \times 10^6$ tumor cells. The HTB group was injected with wildtype cells, the HTB-PC groups was injected with HTB cells that were stably transfected with the pcDNA3.1 empty vector (mock control) and the HTB-HSS1 cells were injected with HTB cells stably transfected with pcDNA3.1-hHSS1. Thus, this figure shows that hHSS1 suppresses anchorage-independent growth and tumorigenicity of U87 cells. Kaplan-Meier analysis of nude mice intracranially injected with $1 \times 10^6$ U87 cells expressing hHSS1 (N=5), U87 wild-type (N=8) or mock-transfected cells (N=5) (Mantel test, P<0.001). Survival and tumor growth were monitored daily.

The ability of transplanted U87 cells to affect survival in immunocompromised mice was evaluated (A172 cells were not studied as these cells are not tumorigenic in mice). Mice implanted with U87 hHSS1-expressing cells survived significantly longer, as compared to those implanted with U87 wild-type cells or cell carrying the empty vector (78 days vs 34 and 30 days for mock-transfected and wildtype cells, respectively; $P<0.0001$; log-rank). This result suggests that hHSS1 decreases the malignancy of U87 cells in vivo (FIG. 4).

hHSS1 alters gene expression profile in stably-transfected U87 cells. The observed growth inhibitory effect of hHSS1, as well as its suppression of tumorigenicity in vitro and in vivo, raises the question of the molecular basis for such phenotypical changes. Comparative gene expression profiling using Affymetrix GeneChip Human Gene 1.0 ST of wild-type (non-transfected), mock-stable-transfected (pcDNA3.1 empty vector) and hHSS1-stable-transfected (pcDNA3.1-hHSS1) U87 cells enabled addressing this question.

Figure 18:
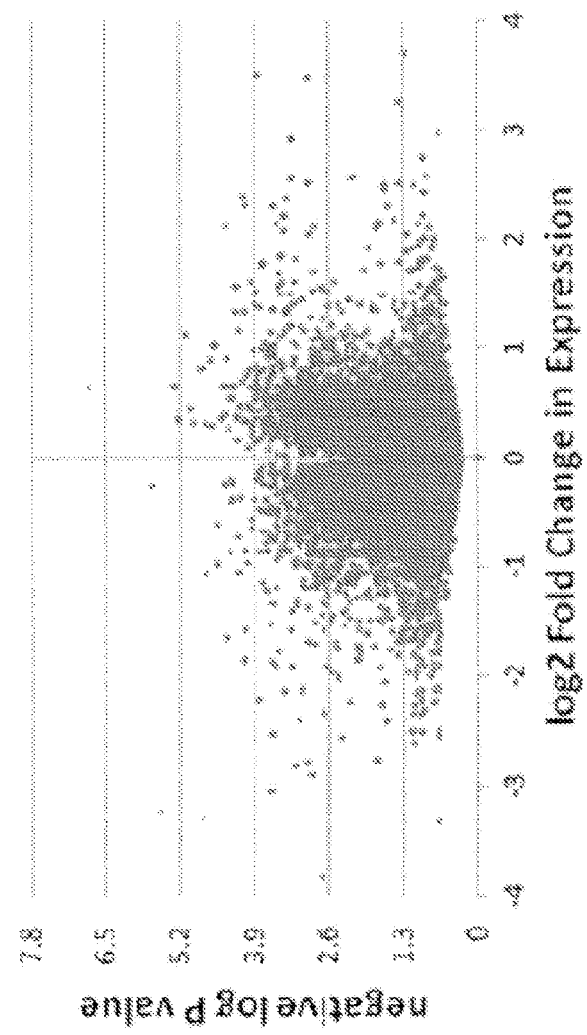
FIG. 18: Shows a volcano plot for 491 differentially hHSS1-regulated genes in U87 stable transfected cells. Values outside −1 and +1 fold change and values above negative log P-value 1.3 (P=0.05) were considered statistically significant down- (left) and up-regulated (right).

Expression profiles of U87, mock and hHSS1-transfected stable cell lines were obtained and compared by two-tailed paired Student's t-test. Differential expression due to the presence of hHSS1 was defined as being statistically significant ($P<0.05$) for the hHSS1-transfected cells compared to both U87 wild-type and the mock transfected controls with the added criterion that difference in gene expression between U87 wild-type and mock transfected cells must not be statistically significant ($P<0.05$). After these stringent criteria were met, 491 genes were found to have altered expression levels of at least two-fold. A volcano plot is shown in FIG. 18. Among these genes were hHSS1 itself which exhibited more than 10-fold increase in expression in the hHSS1 stable-transfected cells compared to mock stable-transfected ($P=0.00013$) and U87 wildtype cells ($P=0.00015$). The expression levels of hHSS1 between U87 wild-type and the mock stable-transfected cells was not statistically significant ($P=0.39$). These findings for hHSS1 in the expression profile analysis are indicative of the integrity of the analysis. Overall, 166 probeset defined genes were up-regulated and 325 were down regulated by at least two-fold demonstrating that hHSS1 expression alters the gene expression profile of U87 cells. Table 1 displays 8 genes up or down-regulated by hHSS1.

TABLE 1

Select genes either up or down-regulated in U87 cells stably expressing hHSS1 as indicated by microarray analysis

| Gene | hHSS1 vs pcDNA3.1 Fold change | hHSS1 vs U87-wild type | P-value hHSS1 vs pcDNA3.1 | U87-wild type vs pcDNA3.1 | U87-wild type vs pcDNA3.1 Fold change |
|---|---|---|---|---|---|
| hHSS1* | +11.7 | 0.00015 | 0.00013 | 0.39 | 1.0 |
| APLN | −14 | 0.0004 | 0.00003 | 0.14 | 1.0 |
| SIK1 | +2.3 | 0.003 | 0.00325 | 0.13 | −1.1 |
| ADAMTS1 | +2.9 | 0.003 | 0.00203 | 0.23 | 1.0 |
| BRCA1 | −2.7 | 0.0002 | 0.00032 | 0.12 | 1.0 |
| BRCA2 | −2.6 | 0.0007 | 0.00051 | 0.7 | −1.1 |
| CDK2 | −2.2 | 0.0008 | 0.00064 | 0.24 | 1.0 |
| CDK6 | −3.1 | 0.001 | 0.00050 | 0.06 | −1.1 |
| ASF1B | −4.5 | 0.00005 | 0.00047 | 0.46 | 1.0 |

Figure 19:
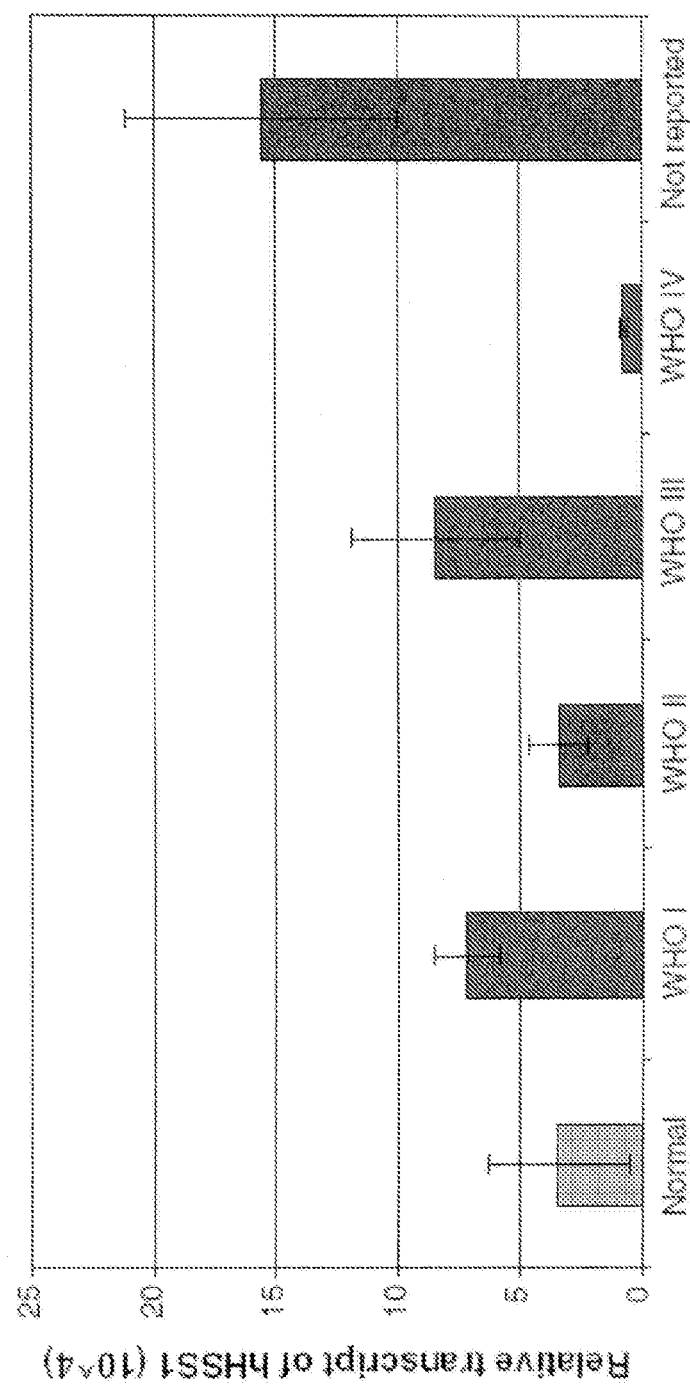
FIG. 19: Shows expression profiles of hHSS1 in WHO-classified brain cancers. TissueScan Brain Cancer Tissue qRT-PCR Array I consisting of 48 human brain tissues was used to determine transcript levels of hHSS1. Data were normalized to b-actin levels. Error bars displays the SEM.
Figure 20:
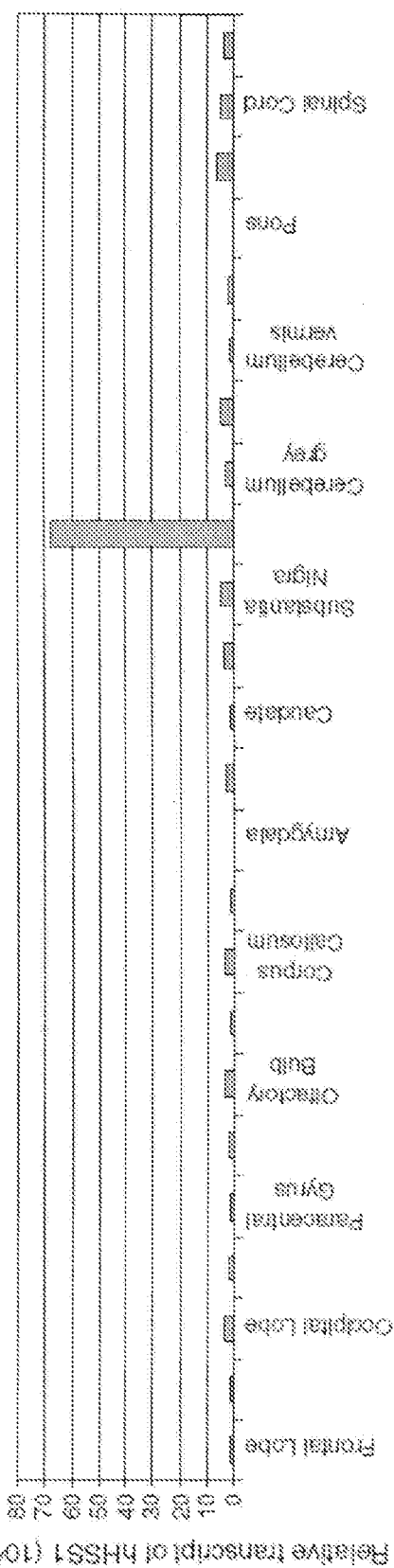
FIG. 20: Shows expression profiles of hHSS1 in human brain tissues (Human Brain Tissue qPCR Panel I). Data were normalized to GAPDH levels.
Figure 21:
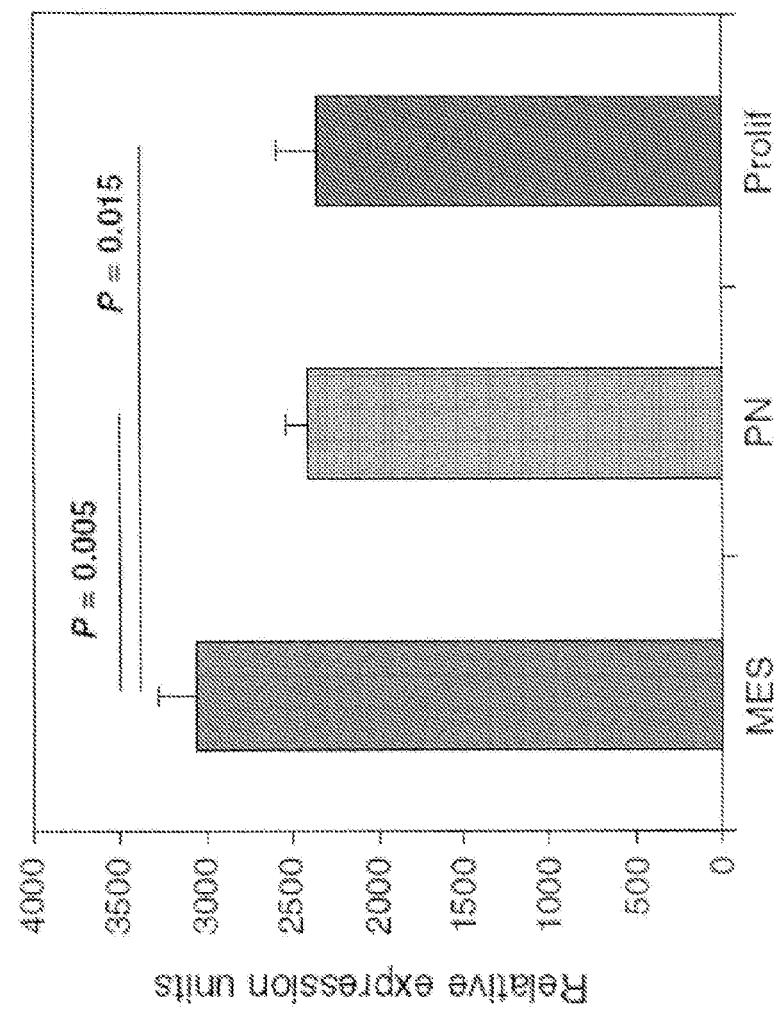
FIG. 21: Shows expression of hHSS1 by glioma molecular subclasses. Expression data from 100 primary gliomas from MD Anderson Hospital patients (GEO accession #GSE4271) were arranged into Mesenchymal (MES; n=35), Proneural (PN; n=37), and Proliferative (Prolif; n=28) groups according to Phillips et al., "Molecular subclasses of high-grade glioma predict prognosis, delineate a pattern of disease progression, and resemble stages in neurogenesis," *Cancer Cell* 9(3):157-173 (2006). hHSS1 probeset (Affymetrix HG-U133, 224727_at) expression was assessed in each group from MASS-normalized data. Statistical differences between groups was evaluated using one-tailed t-test after adjustment for variance, with P values as shown. Mean expression±SEM was as follows: MES, 3057±211; PN, 2408±125; Prolif, 2345±244.

P-values were determined by two-tailed paired Student's t-test.
*Official gene symbol for hHSS1 is C19orf63 hHSS1 expression in glioma-derived tissues. Next, the expression of hHSS1 by transcript profiling in brain cancer and normal brain was examined. The analysis of the Brain Cancer Tissue qPCR Array I showed expression in normal and all tumor grades with a decreased expression of hHSS1 in WHO grade IV (glioblastoma multiform) (FIG. 19). Further, using the Human Brain Tissue qPCR Panel I, hHSS1 expression was found at low levels in normal tissues from various brain regions, with highest levels in pituitary tissue (FIG. 20). Overall, the mRNA level of hHSS1 relative to the reference genes (GAPDH and b-actin) was very low in both surveys.

The distribution of hHSS1 in low-grade diffuse astrocytoma (WHO grade II) and highgrade astrocytoma (glioblastoma multiforme, WHO grade IV) was also evaluated using immunohistochemical analysis. Overall, no obvious detection of hHSS1 was found in normal brain tissue. High expression levels of hHSS1 were found in two out of four grade IV astrocytomas. On the contrary, all four grade II astrocytomas showed low expression of hHSS1. A minimum perivascular staining was also observed, mostly in tumor areas. Although the expression of hHSS1 was predominantly detected in cytoplasm, nuclear stain was seen focally, as observed in A172 cells. Moreover, hHSS1 was detected in some but not all tumor cells. It is important to mention that both sets of primers used in the qRT-PCR and the antibody used to detect hHSS1 do not discriminate between the secreted and membrane bound form of the protein (hHSM1).

hHSS1 expression in glioma molecular subclasses. Since hHSS1 expression was only detectable on a subset of high-grade gliomas, it was considered whether hHSS1 was differentially up-regulated on functionally distinct molecular subclasses of gliomas. Such subclasses are distinguishable by microarray, and include mesenchymal (MES), proneural (PN), and proliferative (Prolif) subclasses. In light of the hHSS1 transfection data, which suggested that hHSS1 expression may alter anchorage-dependent growth and/or cell morphology in vitro, it was particularly intriguing to consider whether hHSS1 was differentially expressed on MES subclass gliomas, which up-regulate genes involved in cell motility and invasiveness. Indeed, relative up-regulation of hHSS1 expression uniquely characterized MES subclass gliomas, which expressed significantly more hHSS1 on microarray than either PN or Prolif subclass gliomas (FIG.

21). Since both MES and Prolif subclasses include de novo high-grade gliomas, whereas the PN subclass is largely devoid of these tumors, this finding further validates the notion that high hHSS1 expression is confined to a subset of high-grade gliomas generally, and to the MES subclass in particular.

After using a 3-D crystallographic protein database to align protein sequences of unknown structure, it was found that a region common to HSS1/HSM1 shares structural homology with TOP-7, which is a non-natural, idealized protein designed in silico for stability at extreme temperature and pH conditions. Kuhlman et al., "Design of a novel globular protein fold with atomic level accuracy," *Science*, 302:1364-1368 (2003). It is, therefore, intriguing to speculate whether HSS1/HSM1 might also exhibit such stability.

Gene expression data from the CGAP database indicates that HSS1 may be involved in numerous cancers, such as brain, colon, eye, liver, lymph node, mammary gland, ovary, prostate and skin. Lal et al., "A public database for gene expression in human cancers," *Cancer Res.*, 59:5403-5407 (1999); Boon et al., "An anatomy of normal and malignant gene expression," *Proc Natl Acad Sci USA*, 99:11287-11292 (2002). Moreover, Mitelman breakpoint data for the gene corresponding to HSS1 indicate that its gene locus is a "hot spot" for chromosomal aberrations implicated in a variety of human cancers (Law et al., "Molecular cytogenetic analysis of chromosomes 1 and 19 in glioma cell Lines," *Cancer Genet Cytogenet*, 160:1-14 (2005)), thereby suggesting a broad role for hHSS1 in cancer.

Figure 22:
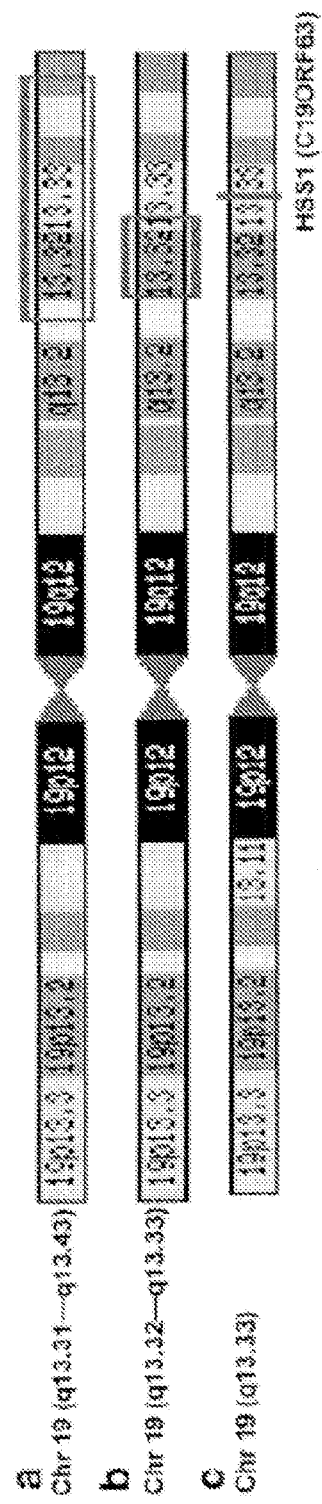
FIG. 22: Shows the mapped position of the putative glioma tumor suppressor at chromosome 19q region. Line a shows Chromosome 19 (q13.31-q13.43), region of the putative glioma tumor suppressor suggested by von Deimling et al., between the markers D19S178 and D19S180 (rectangle in line a). This region includes the hHSS1 gene (C19orf63). Line b shows Chromosome 19 (q13.32-q13.33), region of the putative glioma tumor suppressor gene narrowed by Rubio et al. (smaller rectangle). This region is situated between the loci APOC2 and HRC, which excludes the hHSS1 gene. Line c shows Chromosome 19q13.33, the bar represents the genome location of hHSS1. The UCSC database was used as reference (http://genome.ucsc.edu/cgi-bin/hgGateway).

Upon the discovery of HSS1, only two facts guided the search for a function for this novel protein. First, HSS1 was highly expressed in HSCs and its human genetic locus was at 19q13.33. Since chromosome 19q also harbors at least one gene important for normal glial development and growth regulation as well as for the development of diffuse gliomas, the possibility of a role for hHSS1 in glioma was investigated (Rubio et al., "The putative glioma tumor suppressor gene on chromosome 19q maps between APOC2 and HRC1," *Cancer Res*, 54:4760-4763 (1994); Smith et al., "A transcript map of the chromosome 19q-arm glioma tumor suppressor region," *Genomics*, 64(1):44-50 (2000); and Smith et al., "Mapping of the chromosome 19 q-arm glioma tumor suppressor gene using fluorescence in situ hybridization and novel microsatellite markers," *Genes Chromosom Cancer*, 29:16-25 (2000)). Another suggestive link between hHSS1 and glioma was that the common region for frequent deletions in glioma involves the 19q13.2-13.4 position. Rubio et al., "The putative glioma tumor suppressor gene on chromosome 19q maps between APOC2 and HRC1," *Cancer Res* 54:4760-4763 (1994). This position is situated distal to the D19S178 marker and proximal to the D19S180 marker (Id.; von Deimling et al., "Deletion mapping of chromosome 19 in human gliomas," *Int J Cancer*, 57(5):676-680 (1994)), a region which includes the hHSS1 gene (FIG. 22)

Although chromosome 19q may harbor a potential panglioma tumor suppressor gene, to date, the glioma suppressor genes in this chromosome region remain elusive. Thus, the effect of ectopic expression of hHSS1 on the malignant properties of glioma-derived cells was investigated. The results showed that hHSS1 expression dramatically decreased the growth rate of U87 and A172 glioma-derived cells. In addition, stable expression of hHSS1 in A172 cells strongly inhibited their capacity to grow in low density compared with control cells, which might express endogenous hHSS1 at low levels. The ability to reduce their growth in low density was also observed for U87 cells stably transfected with hHSS1 (data not shown).

It was also striking that U87 cells expressing hHSS1 formed 5.9 times fewer cell aggregates compared to mock-transfected cells. The results also indicate that the expression of hHSS1 may promote growth suppression in U87 cells involving a decrease in growth rate following a decrease in the cell doubling-time.

The expression of hHSS1 also significantly attenuated the colony-forming ability of U87 cells in soft agar matrix, further indicating a possible involvement of hHSS1 in restoration of contact inhibition. In addition, mice injected with U87 cells expressing hHSS1 showed on average greater than 2-fold extension of their life span, indicating that hHSS1 affected the malignant phenotype of glioma-derived cells.

Comparative expression profiling results using Affymetrix gene chip demonstrated that the stable expression of hHSS1 in U87 cells significantly altered its gene expression profile. A substantial number of genes were observed to be either up- or down-regulated by at least two-fold. Presumably genes among this population contribute to the phenotype observed for the hHSS1 stable-transfected cells. Of immediate note and worth mention are the following observations. Apelin was seen as one of the most down-regulated genes in hHSS1-overexpressing cells with an approximate 14-fold decrease in expression. Apelin expression has been observed to be highly up-regulated in the microvasculature in brain tumors. In particular, apelin has been shown to be needed for intersomitic vessel angiogenesis and the promotion of angiogenesis in brain tumors. Kaelin et al., "Paracrine and autocrine mechanisms of apelin signaling govern embryonic and tumor angiogenesis," *Dev Biol*, 305:599-614 (2007). The fact that the expression of apelin is highly down-regulated in the hHSS1-overexpressing cells is consistent with the observed in vivo results where tumor growth was greatly suppressed, thereby leading to a significant increase in survival. It is of further interest that SIK1 (salt inducible kinase 1) gene was among the highly up-regulated genes. This finding is intriguing in that SIK1 has been shown to be a regulator of anoikis and a suppressor of metastasis. Cheng et al., "SIK1 couples LKB1 to p53-dependent anoikis and suppresses metastasis," *Sci Signal*, 2:ra35 (2009). Metastatic tumors generally will avoid anoikis despite loss of adherence. In the case of hHSS1 stable-transfected cells, the increase in SIK1 would presumably correspond to an increase in anoikis and decrease in metastasis, thus suppressing tumor growth and spread. The ADAMTS1 gene was also up-regulated in hHSS1 stable-transfected cells. This metalloproteinase has been found to suppress tumorigenicity and metastasis in model systems. Kuno et al., "The carboxyl-terminal half region of ADAMTS-1 suppresses both tumorigenicity and experimental tumor metastatic potential," *Biochem Biophys Res Commun.*, 319:1327-1333 (2004); Lee et al., "Variable inhibition of thrombospondin 1 against liver and lung metastases through differential activation of metalloproteinase ADAMTS1," *Cancer Res.*, 70:948-956 (2010). Further changes in gene expression to note in hHSS1-overexpressing cells include down-regulation of both BRCA1 and BRCA2 genes, a number of cell cycle associated genes (e.g. CDK2, CDK6), tubulins and the histone chaperone gene ASF1B along with a number of other histone genes.

hHSS1 expression was observed minimally in all 4 low-grade diffuse astrocytomas (WHO grade II) analyzed, while half of the high-grade astrocytomas (glioblastoma multiforme, WHO grade IV) exhibited increased expression. This finding is in agreement with previous reports suggesting a correlation between low-grade gliomas and deletion of 19q13 region (Smith et al., "Localization of common deletion regions on 1p and 19q in human gliomas and their association with histological subtype,". *Oncogene* 18:4144-4152 (1999); this deletion is less common in high-grade gliomas. Moreover, the notion that only a subset of high-grade gliomas over-expresses hHSS1 was further supported by microarray data, which indicated that MES subclass gliomas exclusively up-regulated hHSS1.

hHSS1 is a factor located at 19q13.33 that is involved in suppression of glioma growth. The data described herein demonstrate that hHSS1 is a secreted factor located within a previously defined candidate tumor suppressor gene region at 19q13.33, and that hHSS1 is implicated in the growth inhibition and restoration of the normal contact inhibition properties of glioma-derived cells. Thus, hHSS1 provides novel treatment strategies for cancers such as malignant gliomas.

B. Exemplary Cancers Treatable Using the Methods and Compositions of the Invention As detailed below and herein, many different types of cancers are treatable using the methods and compositions of the invention. The following lists the types of brain cancers that are treatable with the methods of the present invention.

Gliomas: These tumors occur in the glial cells, which help support and protect critical areas of the brain. Gliomas are the most common type of brain tumor in adults, responsible for about 42% of all adult brain tumors. Gliomas are further characterized by the types of cells they affect:

Astrocytoma: Astrocytes are star-shaped cells that protect neurons. Tumors of these cells can spread from the primary site to other areas of the brain, but rarely spread outside the central nervous system. Astrocytomas are graded from I to IV depending on the speed of progression:

Grade I (pilocytic astrocytoma): slow growing, with little tendency to infiltrate surrounding brain tissue. Most common in children and adolescents.

Grade II (diffuse astrocytoma): fairly slow-growing, with some tendency to infiltrate surrounding brain tissue. Mostly seen in young adults.

Grade III (anaplastic/malignant astrocytoma): these tumors grow rather quickly and infiltrate surrounding brain tissue.

Grade IV (glioblastoma multiforme, GBM): an extremely aggressive and lethal form of brain cancer. Unfortunately, it is the most common form of brain tumor in adults, accounting for 67% of all astrocytomas.

Oligodendroglioma: Oligodendrocytes are cells that make myelin, a fatty substance that forms a protective sheath around nerve cells. Oligodendrogliomas, which make up 4% of brain tumors, mostly affect people over 45 years of age. Some subtypes of this tumor are particularly sensitive to treatment with radiation therapy and chemotherapy. Half of patients with oligodendrogliomas are still alive after five years.

Ependymoma: These tumors affect ependymal cells, which line the pathways that carry cerebrospinal fluid throughout the brain and spinal cord. Ependymomas are rare; about 2% of all brain tumors, but are the most common brain tumor in children. They generally don't affect healthy brain tissue and don't spread beyond the ependyma. Although these tumors respond well to surgery, particularly those on the spine, ependymomas cannot always be completely removed. The five-year survival rate for patients over age 45 approaches 70%.

Meningiomas: These tumors affect the meninges, the tissue that forms the protective outer covering of the brain and spine. One-quarter of all brain and spinal tumors are meningiomas, and up to 85% of them are benign. Meningiomas can occur at any age, but the incidence increases significantly in people over age 65. Women are twice as likely as men to have meningiomas. They generally grow very slowly and often don't produce any symptoms. In fact, many meningiomas are discovered by accident. Meningiomas can be successfully treated with surgery, but some patients, particularly the elderly, may be candidates for watchful waiting to monitor the disease.

Acoustic Neuroma/Schwannomas: Schwann's cells are found in the sheath that covers nerve cells. Vestibular schwannomas, also known as acoustic neuromas, arise from the 8th cranial nerve, which is responsible for hearing. Specific symptoms of vestibular schwannoma include buzzing or ringing in the ears, one-sided hearing loss and/or balance problems. Schwannomas are typically benign and respond well to surgery.

Medulloblastoma: Medulloblastoma is a common brain tumor in children, usually diagnosed before the age of 10. These tumors occur in the cerebellum, which has a crucial role in coordinating muscular movements. Some experts believe that medulloblastomas arise from fetal cells that remain in the cerebellum after birth. Tumors grow quickly and can invade neighboring portions of the brain, as well as spreading outside the central nervous system. Medulloblastoma is slightly more common in boys.

C. Overview

Malignant gliomas are a fatal disease with an average life-expectancy following diagnosis of less than one year. Malignant gliomas are also the most common primary human brain tumor, with an estimate of 21,810 new cases and 13,070 deaths in US for the year of 2008 [1]. Loss of heterozygosity studies has shown frequent allelic loss of chromosomes 9p, 10, 13q, 17p, 19q and 22q in astrocytic gliomas and loss of chromosomes 1p and 19q in oligodendroglial and oligoastrocytic gliomas. These data suggest that these chromosome regions contain glioma tumor suppressor genes [2,3]. Furthermore, chromosome 19q loss has been noted consistently in other human tumors [3,5]. These findings suggest that chromosome 19q harbors a potentially pan-glioma and glioma-specific tumor suppressor gene [3,4].

The applicant has identified Hematopoietic Signal peptide containing Secreted 1 (HSS1), and its related membrane-bound splice variant referred to as HSM1. HSS1 is a novel secreted protein discovered in hematopoietic stem cells with gene locus at chromosome 19q13.33. The relevance of that information to this proposal arises from the fact that the 19q13.3-13.4 position is a chromosomal region known to have aberrations or deletions in a variety of solid human tumors, including gliomas [5-10].

To date, many candidate genes have been proposed, but the search is still ongoing for a glioma tumor suppressor located at the 19q13.33 chromosomal region [11, 12]. Interestingly, the HSS1 gene appears to be frequently implicated in a variety of cancers as there have been 1366 reported cases of chromosomes aberrations involving the HSS1 gene locus, which is more than the 846 reported cases for p53 and its gene locus [13]. Moreover, most of the 1366 cases are reported for tissues where the normal gene expression of HSS1 is high, e.g. brain, thyroid, prostate, kidney, pancreas, lung and in various hematopoietic malignancies [13, 14]. Further, SAGE data have shown a significant high probability of HSS1 gene being involved in brain cancer ($P<0.01$) [15].

HSS1 is particularly noteworthy in the context of cancer biology in that it does not possess homology to any known protein and possesses no known domains, rendering it a truly novel protein. Our long term goal is to elucidate the role of HSS1/HSM1 in gliomagenesis, and eventually, to develop novel treatment strategies utilizing HSS1/HSM1 for malignant gliomas.

Glioma is a fatal disease. Malignant gliomas are also the most common primary human brain tumor, with an estimate of 21,810 new cases and 13,070 deaths in US for the year of 2008 [1]. Gliomas cannot be cured. The prognosis for patients with high-grade gliomas is very poor, and is especially so for older patients. Of Americans diagnosed each year with malignant gliomas, about half are alive 1 year after diagnosis, and 25% after two years [16]. Those with anaplastic astrocytoma survive about three years. Glioblastoma multiforme has the worse prognosis with a life expectancy of less than 9-15 months following diagnosis [17,18].

The present invention addressed the unmet need in the art for novel approaches for the treatment of gliomas. Given the fatal effect of various gliomas, it is apparent that novel approaches are needed to increase survival rate of patients diagnosed with this dreaded disease. Current treatment modalities do not substantially increase the survival rate, and certainly are never curative. The standard treatment for gliomas generally consists of a combined approach, using surgery, radiation therapy and chemotherapy [18]. To date, numerous endogenous tumor suppressor proteins have come to light [18]. However, novel treatment modalities that take advantage of endogenous glioma suppressor pathways have not been elucidated. It would seem that perhaps the discovery and use of an endogenous tumor suppressor of glioma, along with conventional therapeutic approaches, such as surgery, radiation and/or chemotherapy, may increase the survival rate for those diagnosed with glioma.

D. The Significance of Genetic Aberrations at 19q, Particularly 19q13.33, in Gliomas Loss of heterozygosity studies have shown frequent allelic loss of chromosomes 9p, 10, 13q, 17p, 19q and 22q in astrocytic gliomas and loss of chromosomes 1p and 19q in oligodendroglial and oligoastrocytic gliomas, suggesting that these loci contain glioma suppressor genes [2.3]. Since chromosome 19q is the only locus lost in all three types of diffuse, malignant human glioma [4], and since loss of 19q has not been noted consistently in other human tumors, these findings suggest that chromosome 19q harbors a potentially pan-glioma or glioma-specific tumor suppressor gene [3,4]. To date, the search for the glioma suppressor gene on chromosome 19q is still ongoing. [3]. The chromosomal location for the putative tumor suppressor of glioma has been further defined to the region at 19q13.33 [11, 12]. Even more specifically, a sub-region of 19q13.33 has been identified by loss of heterozygosity (LOH) analyses. This region putatively harbors a significant suppressor of glioma and maps to a 1.4-1.6 megabase region [12].

E. A Role for HSS1 in the Suppression of Gliomas

HSS1 is a previously uncharacterized, novel secreted factor with no homology to known proteins, nor any known protein domains, which maps to the putative tumor suppressor region on chromosome 19q, specifically at 19q13.33, and more specifically between the genetic markers D19S412 and D19S180. Thus it is likely that HSS1 is the putative tumor suppressor of glioma that is harbored at this chromosomal location. Importantly, we demonstrate herein that HSS1 decreases the proliferation rate of two glioma cells lines (see Section C. Preliminary Results), and appears to restore the normal phenotype by partially overcoming the loss of contact inhibition, a hallmark of gliomas that results in their invasive, and consequently, deadly outcome. Based on these facts, we conclude that HSS1 is a tumor suppressor located on chromosome 19q, specifically at 19q13.33.

F. Properties of HSS1 that Render it Useful as a Possible Therapeutic for Gliomas The discovery of novel human proteins provides new opportunities for the development of therapies for the treatment of diseases. Secreted factors, in particular, are good therapeutic agents as they are accessible to several drug delivery mechanisms, including direct systemic administration. Since HSS1 is a novel secreted protein, which is identified herein as a candidate tumor suppressor of glioma, it may be possible to administer HSS1 directly to the brain via intracerebroventricular injection as a treatment for glioma. Thus, the elucidation of the tumor suppression properties of HSS1 may provide novel opportunities to develop treatment strategies for malignant gliomas.

G. Compositions

Also encompassed by the invention are pharmaceutical compositions useful in the methods of the invention. The compositions comprise HSS1, HSM1, or a combination thereof. The compositions can additionally comprise one or more (e.g., at least one) pharmaceutically acceptable carrier.

The compositions can also comprise a peptide having at least about 80% homology to HSS1, a peptide having at least about 80% homology to HSM1, or any combination thereof. In yet additional embodiments, the peptide can have at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% homology to HSS1. In yet additional embodiments, the peptide can have at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% homology to HSM1.

The invention additionally encompasses pharmaceutical compositions comprising a fragment of HSS1, HSM1, or any combination thereof. The terms "HSS1 fragment" and "HSM1 fragment" refer to a peptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least about 4 amino acids in length. As noted above, the full-length cDNA sequence of HSS1 consists of approximately 1.9 kb containing an open reading frame of 789 bp (e.g., corresponding to about 263 amino acids). In other embodiments of the invention, the HSS1 fragment and/or HSM1 fragment has a size of about 5 amino acids, about 6 amino acids, about 7 amino acids, about 8 amino acids, about 9 amino acids, about 10 amino acids, about 11 amino acids, about 12 amino acids, about 13 amino acids, about 14 amino acids, about 15 amino acids, about 16 amino acids, about 17 amino acids, about 18 amino acids, about 19 amino acids, about 20 amino acids, about 25 amino acids, about 30 amino acids, about 35 amino acids, about 40 amino acids, about 45 amino acids, about 50 amino acids, about 55 amino acids, about 60 amino acids, about 65 amino acids, about 70 amino acids, about 75 amino acids, about 80 amino acids, about 85 amino acids, about 90 amino acids, about 95 amino acids, about 100 amino acids, about 105 amino acids, about 110 amino acids, about 115 amino acids, about 120 amino acids, about 125 amino acids, about 130 amino acids, about 135 amino acids, about 140 amino acids, about 145 amino acids, about 150 amino acids, about 155 amino acids, about 160 amino acids, about 165 amino acids, about 170 amino acids, about 175 amino acids, about 180 amino acids, about 185 amino acids, about 190 amino acids, about 195 amino acids, about 200 amino acids, about 205 amino acids, about 210 amino acids, about 215 amino acids, about 220 amino acids, about 225 amino acids, about 230 amino acids, about 235 amino acids, about 240 amino acids, about 245 amino acids, about 250 amino acids, about 255 amino acids, or about 260 amino acids. Preferably, the fragment spans at least one epitope of the full-length HSS1 or HSM1.

The pharmaceutical composition of the invention can be formulated into any suitable dosage form. Exemplary dosage forms for pharmaceutical administration are described herein. Examples include but are not limited to liquids, injectables, ointments, creams, emulsions, lotions, gels, bioadhesive gels, sprays, aerosols, pastes, foams, capsules, microcapsules, suspensions, pessary, powder, semi-solid dosage form, etc.

The pharmaceutical compositions may be formulated for immediate release, sustained release, controlled release, delayed release, or any combinations thereof. The pharmaceutical compositions for administration may be administered in a single administration or in multiple administrations.

The compositions of the invention comprise a therapeutically effective amount of HSS1, HSM1, a HSS1 fragment, a HSM1 fragment, a peptide having at least about 80% homology to HSS1 (or a % homology as defined above), a peptide having at least about 80% homology to HSM1 (or a % homology as defined above), or any combination thereof (collectively referred to as "HSS1 peptides and HSM1 peptides"). By the phrase "therapeutically effective amount" it is meant any amount of the HSS1 peptides and/or HSM1 peptides that are effective in preventing, treating or ameliorating a cancer, and in particular a brain cancer. Complete cure is not required, though is encompassed by the present invention.

Additional compounds or excipients suitable for use in the pharmaceutical compositions of the invention of the invention include but are not limited to one or more solvents, binding agents, filling agents, lubricating agents, suspending agents, sweeteners, flavoring agents, preservatives, buffers, wetting agents, disintegrants, effervescent agents, bulking agents, coloring agents, pH adjuster, buffers, chelating agents, and other excipients. Such excipients are known in the art.

Suitable preservatives in the pharmaceutical compositions of the invention include, but are not limited to, potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride, cetylpyridinium chloride, chlorhexidine, imidazolidinyl urea, phenol, potassium sorbate, benzoic acid, bronopol, chlorocresol, paraben esters, phenoxyethanol, sorbic acid, alpha-tocophernol, ascorbic acid, ascorbyl palmitate, butylated hydroxyanisole, butylated hydroxytoluene, sodium ascorbate, sodium metabisulphite, citric acid, edetic acid, semi-synthetic derivatives thereof, and combinations thereof. Other suitable preservatives include, but are not limited to, benzyl alcohol, chlorhexidine (bis(p-chlorophenyldiguanido) hexane), chlorphenesin (3-(-4-chloropheoxy)-propane-1,2-diol), Kathon CG (methyl and methylchloroisothiazolinone), parabens (methyl, ethyl, propyl, butyl hydrobenzoates), phenoxyethanol (2-phenoxyethanol), sorbic acid (potassium sorbate, sorbic acid), Phenonip (phenoxyethanol, methyl, ethyl, butyl, propyl parabens), Phenoroc (phenoxyethanol 0.73%, methyl paraben 0.2%, propyl paraben 0.07%), Liquipar Oil (isopropyl, isobutyl, butylparabens), Liquipar PE (70% phenoxyethanol, 30% liquipar oil), Nipaguard MPA (benzyl alcohol (70%), methyl & propyl parabens), Nipaguard MPS (propylene glycol, methyl & propyl parabens), Nipasept (methyl, ethyl and propyl parabens), Nipastat (methyl, butyl, ethyl and propyel parabens), Elestab 388 (phenoxyethanol in propylene glycol plus chlorphenesin and methylparaben), and Killitol (7.5% chlorphenesin and 7.5% methyl parabens).

Examples of filling agents are lactose monohydrate, lactose anhydrous, and various starches; examples of binding agents are various celluloses and cross-linked polyvinylpyrrolidone, microcrystalline cellulose, such as Avicel® PH101 and Avicel®. PH102, microcrystalline cellulose, and silicified microcrystalline cellulose (ProSolv SMCC).

Suitable lubricants, including agents that act on the flowability of the powder to be compressed, are colloidal silicon dioxide, such as Aerosil® 200, talc, stearic acid, magnesium stearate, calcium stearate, and silica gel.

Examples of sweeteners are any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel® PH 101 and Avicel® PH 102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The invention is further described by reference to the following examples, which are provided for illustration only. The invention is not limited to the examples, but rather includes all variations that are evident from the teachings provided herein. All publicly available documents referenced herein, including but not limited to U.S. patents, are specifically incorporated by reference.

EXAMPLES

Example 1

Isolation of HSS1 cDNA

The murine form of HSS1 (mHSS1) was isolated via PCR from a lineage-negative mouse bone marrow cDNA library. (Zhao et al., Blood, 96:3016-3022 (2000)). The human form of HSS1 (hHSS1) was isolated from a cDNA human testis library (Human MTC Multiple Tissue cDNA Panel II, Clontech). Primers were based upon predicted gene sequences and PCR products were sequenced to confirm the DNA sequence of both human and mouse HSS1 genes.

Cell Culture and hHSS1 Expression Vector Construct:

Human embryonic kidney 293T and A172 glioma cell lines (ATCC, Manassas, Va. USA) were cultured in DMEM supplemented with 10% FBS. The human U87 glioma cell line (ATCC HTB-14) was maintained in alpha-MEM supplemented with 10% FBS, non-essential amino acids, sodium pyruvate and sodium bicarbonate. The pTT3-hHSS1 expression construct was kindly provided by Dr. W. French Anderson. The hHSS1 cDNA was subcloned from pTT3 vector into the EcoRI and HindIII sites of pcDNA.3.1 mammalian expression vector (Invitrogen, Carlsbad, Calif., USA). The construct had a 6-His tag in-frame fused at the C-terminal of hHSS1 gene. The resultant construct pcDNA3.1-hHSS1 was verified by sequencing analysis.

Example 2

Functional Characterization of HSS1—a Novel Protein with No Known Homology to Other Known Proteins or Other Known Protein Domains with Functional Properties of a Candidate Tumor Suppressor HSS1 is not Expressed in the A172 and U87 Glioma-Derived Cell Lines:

Since HSS1 is located at a chromosomal region known to have aberrations or deletions in a variety of gliomas, the inventors investigated whether HSS1 could affect the malignant properties of two well-studied human glioma-derived cell lines, namely A172 and U87, by using cell proliferation and soft agar assays. The inventors chose these cell lines as the subject of their investigations because a previous report suggested that the broad region corresponding to the gene locus of HSS1 at 19q13.33 was deleted in these glioblastoma cell lines [22]. Moreover, this report concluded that the A172 and U87 cell lines contained 19q deletions similar to those found in sporadic human gliomas, and as such would be useful for evaluating the function of putative 19q glioma tumor suppressor genes.

Summary:

Because HSS1 was found to be expressed in normal brain tissues [14], the inventors first sought to confirm whether HSS1 was expressed in the two glioma-derived cell lines under investigation. By using gene specific primers in a one-step RT-PCR reaction, the inventors determined that these cells did not express HSS1 (FIG. 1, lanes 1 and 2). After determining that HSS1 was not expressed in the A172 and U87 glioma-derived cell lines, the inventors stably transfected these cell lines with a construct carrying human HSS1 cDNA (pcDNA3.1-hHSS1) or with the empty vector as control to assess the effect of HSS1 expression on various tumor-associated properties of these cells. Non-transfected wildtype glioma cells also served as control. The expression of hHSS1 following transfection was confirmed by using RT-PCR (FIG. 1, lanes 2 and 5). The results showed that while human HSS1 mRNA was not detectable in the control cells, the selected pcDNA3.1-hHSS1-transfected clonal cells stably expressed the HSS1 mRNA.

Stable Expression of HSS1 in the A172 and U87 Glioma-Derived Cell Lines Decreases the Tumorgeneic Phenotype by Decreasing Cell Growth and Restoring Responsiveness to Contact Inhibition: Stable Expression of HSS1 in the A172 and U87 Glioma-Derived Cell Lines Decreases Cell Growth.

During the selection of the stable clones, the inventors first observed that the growth of the pcDNA3.1-hHSS1 transfected cells was dramatically different relative to mock transfected clones. Thus, the inventors further performed cell counting and colony forming ability assays to evaluate the proliferation rate of cells non-transfected and transfected with pcDNA3.1-hHSS1 or the mock control vector. The results showed that U87 and A172 HSS1-expressing glioma cells significantly decreased their cell number 4.5-fold and 3-fold, respectively compared to mocktransfected cells. See FIGS. 2a and 3a, respectively, for the results with the U87 and A172 cell lines.

Stable Expression of HSS1 in the A172 and U87 Glioma-Derived Cell Lines Dramatically Decreases Colony Formation and the Number of Cellular Aggregates, Respectively.

The inventors further observed that in the case of the U87 glioma cell line, which has properties of both a glioblastoma and astrocytoma, cell aggregate formation was a discernable property of the phenotype of this cell line, as compared to the A172 cell line. The formation of aggregates in this cell line may reflect the degree of loss of contact inhibition in these cells. Thus, the inventors sought to discern the difference in the number of aggregates formed for the U87 cell line for the stable clone expressing HSS1, the clone transfected with the mock vector and the wild type cell. The number of cell aggregates formation in U87 cells expressing HSS1 was 6.7 and 8.3 times less frequent relative to mocktransfected and wild type cells, respectively (FIGS. 2(b) and 2(c)).

Since for the A172 cell line, which has the properties of a glioblastoma, there were no observable aggregates formed, the inventors assessed the difference in colony-forming ability for this cell line as an additional measurement of proliferation rate. The inventors observed that the number of colonies formed for A172 cells expressing HSS1 was also dramatically less as compared to the mock vector or wild type cell controls (See FIG. 3b).

Stable Expression of HSS1 in the Glioma-Derived Cell Line, U87, Produces a Less Tumorgeneic Phenotype by Restoring the Normal Cell Property of Contact Inhibition.

To evaluate the ability of U87 cells expressing HSS1 to grow in an anchorage-independent manner, $8 \times 10^4$ cells were mixed with a 0.33% top agarose suspension, which was then layered onto a 0.5% bottom agarose. Each assay was performed in triplicates. The plates were incubated at 37° C. for 23 days, after that, nine fields of each plate was photographed and the colony number counted manually. The results show that either U87 wild-type cells or U87 cell transfected with the mock vector, both of which do not express HSS1, formed numerous colonies in soft agar compared to HSS1-expressing cells (See FIGS. 2(d) and 2(e)). Moreover, the size of the colonies observed for the non-transfected wild type or the mock transfected cells were markedly larger compared to that observed for cells expressing HSS1. These results suggest that stable expression of HSS1 in cells where the gene had been absent produces a less tumorgeneic phenotype by restoring the normal cell property of contact inhibition.

Conclusion:

Taken together, these results suggest that in glioma-derived cells that do not express HSS1, stable expression of HSS1 in these cells is capable of reversing some of the properties of the malignant phenotype.

Example 3

Transient Transfection and Immunoblotting

Following the cell culture from Example 1, supernatants containing the hHSS1 protein were produced by transient transfection of 293T cells harvested after 48 h post-transfection using the Calcium Phosphate Transfection kit (Invitrogen) and 4 μg of plasmid DNA purified with a Qiagen column (Qiagen, Valencia, Calif., USA). Conditioned media from 293T cells were harvested, concentrated using a Macrosep centrifugal device (Pall, East Hills, N.Y., USA) and stored in aliquots at 4° C. Protein expression was confirmed by Western blot in both supernatant and cell lysate prepared from $2 \times 10^5$ cells using a standard protocol and mass spectrometry. An anti-His (C-term)-HRP antibody (Invitrogen) allowed detection of hHSS1 protein by Western blot. Immunoreactive bands were visualized by colorimetric detection using TMB solution (Invitrogen). The glycosylation pattern of HSS1 was assessed by treating cell lysates with PNGase F, Sialidase and O-glycanase.

Detection of hHSS1-mRNA by reverse transcription (RT)-PCR.

Total RNA was isolated from A172 and U87 cell lines using the RNeasy minikid (Qiagen). The RT-PCR reaction was carried out by using SuperScrip III One-Step RT-PCR (Invitrogen) and 1 μg of total RNA. The primers specific for HSS1 were 5'TCCTGCTCTTGCTGATGG-3' (SEQ ID NO: 1) (forward); 5'-GAGACATAGCCACCAGCTTC-3' (SEQ ID NO: 2) (Reverse). The conditions of the reaction were those suggested by the manufacturer. A GAPDH mRNA control was also amplified by PCR according to the manufacturer. PCR products were then checked via agarose gel electrophoresis.

Selection of Stable Transfections.

The glioblastoma-derived A172 and U87 cell lines were transfected as mentioned above, either with pcDNA3.1-hHSS1 or pcDNA3.1 empty vector. After 24 h, 800 μg ml$^{-1}$ of G-418 (Invitrogen) was added to the culture. Stable selection was performed for 4-8 weeks and the stably transfected clones were then expanded and cryopreserved in aliquots for further use. The expression of hHSS1 mRNA was confirmed using RT-PCR.

Quantitative Proliferation Assay.

Cell viability was measured by cell counting using trypan blue exclusion on wild-type (untransfected cells), on pcDNA3.1 empty vector, and pcDNA3.1-hHSS1 clones. U87 cells ($8 \times 10^4$) were plated in triplicate in 10 cm plates and incubated at 37° C., 5% $CO_2$. After 6 days, the number of cells was quantified and the values were expressed as means. Also, $5 \times 10^3$ U87 cells were seeded in septuplicate in 96-well plates and after 3 days of incubation the number of cell aggregates formed was determined in the central field of each well. A172 cells ($8 \times 10^4$) were plated in triplicate in 10 cm plates and after 7 days the cells were harvested and counted. To test the plating efficiency of A172 cells, $2 \times 10^3$ A172 cells were seeded in triplicate in 10-cm plates. After 23 days, cell colonies were stained for 1 h with 0.001% neutral red (Sigma-Aldrich, St. Louis, Mo., USA) in PBS, after that, plates were photographed. At least two experiments using each assay were performed.

Growth Inhibition of Cells.

U87 and A172 wild-type cells, pcDNA3.1 and pcDNA-hHSS1 cells were seeded at a density of $9 \times 10^4/2$ ml medium in 6-well plates in triplicate. Over the course of 8 days, cells were harvested and counted by trypan blue dye exclusion.

qRT-PCR.

For the analysis of hHHS1 expression in brain cancer tissue, the inventors used the TissueScan Brain Cancer Tissue qPCR Array I-HBRT102 (Origene Technologies, Rockville, Md., USA) consisting of 48 human brain tissue normalized against β-actin gene. This array included meningiomas, oligodendroglioma and astrocytomas. Normal brain tissue was also evaluated using Human Brain Tissue qPCR Panel 1-HBRT101 (Origene Technologies), consisting of 24 human brain tissues normalized against GAPDH gene. qRT-PCR was performed using SYBR Green PCR master mix (Roche Diagnostics, (Indianapolis, Ind., USA) using primers specific for hHSS1 (forward 5'CAGCAGGATGGTACCTTGTC-3' (SEQ ID NO: 3)) and reverse (5'GAGACATAGCCAC-CAGCTTC-3' (SEQ ID NO: 2)). Relative mRNA levels of hHSS1 were calculated using the LightCycler 480 Relative Quantification Software 1.2 (Roche Diagnostics).

Immunocytochemical and Immunohistochemical Analysis.

hHSS1 was detected in U87 and A172 cells stably expressing hHSS1 and in formalin-fixed paraffin-embedded tissue sections of glioma tumors. U87 and A172 cells ($4 \times 10^4$ cells) were cultured overnight in 4-well chamber slides coated with 5 μg/ml fibronectin. Cultures were fixed in cold methanol for 10 min. at −20° C. Tissue sections from four low grade diffuse astrocytomas (WHO grade II) and four high-grade astrocytomas (glioblastoma multiform, WHO grade IV) were incubated in AquaDepar (Biocare Medical, Concord, Calif.) reagent at 70° C. for 10 min. After deparaffinization, antigen retrieving was performed by using Reveal reagent (Biocare Medical). To block non-specific protein staining, culture and sections were incubated in background sniper (Biocare Medical) for 10 min. hHSS1 was detected by incubation for 2 h with a custom made rabbit polyclonal antibody anti-hHSS1 serum raised against synthetic peptide corresponding to amino acids 108-123 using 1:250 and 1:40 dilution for cultures and tissue sections, respectively (Genescript, Piscataway, N.J.). This step was followed by incubation for 1 h at RT in-ImmPRESS reagent anti-rabbit Ig Peroxidase (Vector Laboratories, Burlingame, Calif.) and 30 min incubation in ImmPact AEC Peroxidase Substrate (Vector Laboratories). Slides were further counterstained with hematoxylin. Negative control included a stain containing all components except the hHSS1 primary antibody. The presence of hHSS1 was visualized by a reddish brown precipitate. The specificity of the hHSS1 polyclonal antibody was previously verified by Western blot analysis.

Anchorage-Independent Growth on Soft Agar.

Medium containing U87 cells ($8 \times 10^4$) was mixed with a 0.33% low-melting agarose top suspension, which was then layered onto a 0.5% bottom agarose. Each assay was performed in triplicate. The plates were incubated at 37° C., 5% $CO_2$ for 23 days; after that, nine fields of each plate were photographed and colonies were counted manually.

Intracranial Xenograft in Immunodeficient Mice.

Tumorigenicity in vivo was determined by intracranial injection of U87 glioma-derived cells in male Nu/Nu mice, age 6 weeks (Charles River Laboratories, Wilmington, Mass., USA). Mice were quarantined for one week before initiation of the experimental procedure. Initially, mice were anesthetized with isoflurane (FORANE®). The skin was then cut using a scalpel and retracted for skull exposure. Skulls were punctured with a bone penetrator approximately 2 mm posterior to Bregna. After skull puncture, 10 μl of a $1 \times 10^6$ cell suspension in PBS was injected with a 100 μl syringe containing a blunt end needle. The skin was replaced over the skull puncture and given two stitches. Mice subsequently recovered from the anesthesia within minutes and became mobile and active. No apparent ill effects were observed immediately after the cell injection. Three groups of mice were studied: U87 wild-type cells (N=8), pcDNA3.1 (N=5) and pcDNA3.1-hHSS1 (N=5). All mice were properly treated in accordance with guidelines of the Institutional Animal Care and Use Committee (IACUC) at the BATTS Laboratories facility (Northridge, Calif., USA).

Transcript Expression Profiling Using Microarray.

Affymetrix Genechip Human Gene 1.0 ST Array was used to obtain transcript expression profiles in wild type (non-transfected), mock stable-transfected (pcDNA3.1 empty vector), and hHSS1-stable-transfected (pcDNA3.1-hHSS1) U87 cells. Exponentially growing U87 cells at growth curve day 4 were harvested by trypsinization and the total RNA was isolated using the RNeasy minikit (Qiagen). Further RNA characterization and chip analysis was carried out at the Functional Genomics Core of the City of Hope (Duarte, Calif. USA). Samples were evaluated in triplicate. Expression values were determined using dChip (Jul. 9, 2009 build). For glioma tissue microarray, 100 primary gliomas from MD Anderson Hospital patients (GEO accession #GSE4271) were arranged into Mesenchymal, Proneural, and Proliferative subclasses according to Phillips et al., Cancer Cell, 9(3): 157-173 (2006). hHSS1 probeset expression (Affymetrix HG-U13 probeset, 224727 at) was then assessed in each group form MASS-normalized data, and statistical differences between groups evaluated using one-tailed student's t-test after adjustment for variance.

Statistical Analysis.

For the proliferation assays, two-tailed Student's t-tests were performed to establish the statistical significance of differences between control cells and hHSS1—expressing cells. Differences among groups in the growth curve analysis were determined by two-way analysis of variance (ANOVA) with Tukey's test for pairwise post-hoc comparisons. Survival analysis was performed by the Kaplan-Meier test. Differences were considered statistically significant when $P<0.05$.

Results.

Bioinformatics, cloning, and sequencing of HSS1 and HSM1. Using Affymetrix microarray analysis, approximately 900 highly and/or differentially expressed genes were identified from three subsets of murine HSC populations. Zhong et al., PNAS USA, 102:2448-2453 (2005). Probe sets with significant expression in the HSC subsets of unknown gene products were subjected to BLAT analysis and examined for correspondence to novel in silico predicted genes. Predicted genes identified in this manner were then subjected to analysis for signal peptides using Signal P (http://www.cbs.dtu.dk/services/TMHMM/). In this manner, novel secretable proteins were identified. Gene expression corresponding to one probe (96320_at) found in all three stem cell subsets identified a downstream untranslated region of a predicted gene on mouse chromosome 7 (GenScan chr7__6.156) and on human chromosome 19 (GenScan NT_011109.821). The respective mouse and human gene predictions specified proteins with 86% identity to each other, neither of which was existent in the databank. These mouse and human genes predicted a signal peptide sequence, but no transmembrane domain, indicating that the sequences coded for secreted proteins. Both mouse and human genes were cloned from their respective mouse and human cDNA libraries via PCR using primers based upon the gene predictions. The clones were then sequenced and the predicted sequences were confirmed for both human and mouse. The secretable form of the gene was designated HSS1 (FIG. 5). The mouse and human gene ID's are 69683 and 284361, respectively.

Example 4

Table 2 below shows a subset of 5 down and up-regulated genes in A172 cells stably expressing hHSS1 relative to pcDNA3.1 mock-transfected control as indicated by microarray analysis.

TABLE 2

| Gene | Description | Fold Change | NCBI | Locus |
| --- | --- | --- | --- | --- |
| CCL2 | Chemokine (C-C motif) ligand 2 | −2.025 | NM_002982 | 17q11.2-q12 |
| PCOLCE | Procollagen C-endopeptidase enhancer | −2.653 | NM_002593 | 7q22 |
| MGST1 | microsomal glutathione S-transferase 1 | −2.451 | NM_145792 | 12p12.3-p12.1 |
| RASGRP1 | RAS guanyl releasing protein 1 (calcium and DAG-regulate | +2.821 | NM_005739 | 15q14 |
| SULF 1 | Sulfatase 1 | +2.958 | NM_001128205 | 8q13.2-q13.3 |

Comparative expression profiling results using Affymetrix gene chips demonstrated that the stable expression of hHSS1 in A172 cells up- or down-regulated, by at least two-fold, genes involved in tumorigenesis, invasiveness and metastasis (Table 1). CCL2 was seen as one of the downregulated genes in hHSS1-overexpressing cells with an approximate 2-fold decrease in expression. CCL2 has been shown to be an active mediator of the tumorigenesis and metastasis of several solid tumors, including a role in regulating the migration and proliferation of breast cancer, multiple myeloma and prostate cancer. (Loberg et al., "CCL2 as an important mediator of prostate cancer growth in vivo through the regulation of macrophage infiltration," Neoplasia, 9:556-62 (2007).) Expression of CCL2 was correlated with advanced stage and it was shown that prostate cancer cells produced CCL2 in vitro, which mediated proliferation and invasion in an autocrine/paracrine manner. Downregulation of CCL2 in hHSS1-overexpressing cells is consistent with the observed in vivo results where tumor growth was greatly suppressed, thereby leading to a significant increase in survival.

MGST1 is a membrane bound GST in the outer membrane of mitochondria that is up-regulated in several tumor tissues and it has been involved in anticancer drug resistance. (Johansson et al., "Microsomal glutathione transferase 1 in anticancer drug resistance," Carcinogenesis, 28:465-70 (2007).) The data presented herein indicates that HSS1 expression is down regulating MGST1 which can protect the cells from several cytostatic drugs.

HSS1 expression down-regulated the PCOLCE expression, which is a strong inhibitor of matrix metalloproteinase. Expression of metalloproteinase and tissue inhibiting metalloproteinase (TIMP) has been shown to increase in some tumor cell lines. (Mott et al, "Post-translational proteolytic processing of procollagen C-terminal proteinase enhancer releases a metalloproteinase inhibitor," J. Biol. Chem., 275 (2):1384-1390 (2000).) Several studies have shown that the increase in the expression of TIMP can decrease the invasiveness of some tumor cell lines.

HSS1 also down-regulated SULF1 and RASGRP1 expression, SULF1 if found to inhibit the tumorigenesis of hepatocellular carcinoma cell lines in vitro and in vivo by down regulation of FGF-2 and VEGF and up-regulation of HDAC inhibitors. (LaiDalbir et al., "The tumor suppressor function of human sulfatase 1 (SULF1) in carcinogenesis," J. Gastrointest. Cancer, 39(1-4):149-158 (2008).) RasGRP1 is a guanine nucleotide exchange factor that activates Ras GTPases and is activated downstream of antigen receptors on both T and B lymphocytes. Ras-GRP1 provides signals to immature T cells that confer survival and proliferation, but RasGRP1 also promotes T cell receptor-mediated deletion of mature T cells. It has been shown that a 2-fold elevation in RasGRP1 expression markedly increased apoptosis of WEHI-231 cells following B cell receptor ligation. Elevated RasGRP1 expression caused down-regulation of NF-kappaB and Bcl-x(L), which provide survival signals counter-acting apoptosis induction by B cell receptor. (Guilbault et al., "Ras-GRP1 sensitizes an immature B cell line to antigen receptor-induced apoptosis," *J. Biol. Chem.,* 279(19):19523-30 (2004)).

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

The invention claimed is:

1. A method for treating a brain cancer that is glioblastoma or astrocytoma, comprising administering via intracerebroventricular infusion to the brain of a subject in need of treatment of glioblastoma or astrocytoma an effective amount of Hematopoietic Signal peptide-containing Secreted 1 (HSS1) comprising SEQ ID NO: 6.

2. The method of claim 1, wherein the brain cancer is a primary brain cancer that is glioblastoma or astrocytoma.

3. The method of claim 1, wherein the HSS1 is delivered before or after radiation therapy.

4. The method of claim 1, wherein the HSS1 is delivered before or after brain surgery to remove all or part of the cancerous tissue.

5. The method of claim 1, wherein the HSS1 is delivered before or after chemotherapy.

6. The method of claim 1, wherein the subject treated with the HSS1 has increased survival following treatment.

7. The method of claim 1, wherein treatment with the HSS1 results in a reduction in mass of the glioblastoma or astrocytoma.

8. The method of claim 1, wherein an effective and safe dose of the HSS1 is administered to the subject in need of treatment of glioblastoma or astrocytoma.

9. A method for treating a brain cancer that is glioblastoma or astrocytoma, comprising administering via intracerebroventricular infusion to the brain of a subject in need of treatment of glioblastoma or astrocytoma an effective amount of a peptide having at least about 95% homology to Hematopoietic Signal peptide-containing Secreted 1 (HSS1) comprising SEQ ID NO: 6.

* * * * *

SEQUENCE LISTING

```
<160> NUMBER OF SEQ ID NOS: 8

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tcctgctctt gctgatgg                                                   18

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gagacatagc caccagcttc                                                 20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cagcaggatg gtaccttgtc                                                 20

<210> SEQ ID NO 4
<211> LENGTH: 262
<212> TYPE: PRT
<213> ORGANISM: Homo sapiens

<400> SEQUENCE: 4

Met Ala Ala Ala Ser Ala Gly Ala Thr Arg Leu Leu Leu Leu Leu Leu
1               5                   10                  15

Met Ala Val Ala Ala Pro Ser Arg Ala Arg Gly Ser Gly Cys Arg Ala
                20                  25                  30

Gly Thr Gly Ala Arg Gly Ala Gly Ala Glu Gly Arg Glu Gly Glu Ala
            35                  40                  45

Cys Gly Thr Val Gly Leu Leu Leu Glu His Ser Phe Glu Ile Asp Asp
    50                  55                  60

Ser Ala Asn Phe Arg Lys Arg Gly Ser Leu Leu Trp Asn Gln Gln Asp
65                  70                  75                  80

Gly Thr Leu Ser Leu Ser Gln Arg Gln Leu Ser Glu Glu Glu Arg Gly
                85                  90                  95
```

```
Arg Leu Arg Asp Val Ala Ala Leu Asn Gly Leu Tyr Arg Val Arg Ile
            100                 105                 110

Pro Arg Arg Pro Gly Ala Leu Asp Gly Leu Glu Ala Gly Gly Tyr Val
            115                 120                 125

Ser Ser Phe Val Pro Ala Cys Ser Leu Val Glu Ser His Leu Ser Asp
            130                 135                 140

Gln Leu Thr Leu His Val Asp Val Ala Gly Asn Val Val Gly Val Ser
145                 150                 155                 160

Val Val Thr His Pro Gly Gly Cys Arg Gly His Glu Val Glu Asp Val
                165                 170                 175

Asp Leu Glu Leu Phe Asn Thr Ser Val Gln Leu Gln Pro Thr Thr
            180                 185                 190

Ala Pro Gly Pro Glu Thr Ala Ala Phe Ile Glu Arg Leu Glu Met Glu
            195                 200                 205

Gln Ala Gln Lys Ala Lys Asn Pro Gln Glu Gln Lys Ser Phe Phe Ala
            210                 215                 220

Lys Tyr Trp Met Tyr Ile Ile Pro Val Val Leu Phe Leu Met Met Ser
225                 230                 235                 240

Gly Ala Pro Asp Ala Gly Gly Gln Gly Gly Gly Gly Gly Gly
                245                 250                 255

Gly Gly Gly Ser Gly Arg
            260

<210> SEQ ID NO 5
<211> LENGTH: 258
<212> TYPE: PRT
<213> ORGANISM: Mus musculus

<400> SEQUENCE: 5

Met Val Ala Ala Gly Ala Gly Val Thr Arg Leu Leu Val Leu Leu Leu
1               5                   10                  15

Met Val Ala Ala Pro Ser Arg Ala Arg Gly Ser Gly Cys Arg Val
            20                  25                  30

Gly Ala Ser Ala Arg Gly Thr Gly Ala Asp Gly Arg Glu Ala Glu Gly
            35                  40                  45

Cys Gly Thr Val Ala Leu Leu Leu Glu His Ser Phe Glu Leu Gly Asp
50                  55                  60

Gly Ala Asn Phe Gln Lys Arg Gly Leu Leu Leu Trp Asn Gln Gln Asp
65                  70                  75                  80

Gly Thr Leu Ser Ala Thr Gln Arg Gln Leu Ser Glu Glu Glu Arg Gly
            85                  90                  95

Arg Leu Arg Asp Val Ala Ala Val Asn Gly Leu Tyr Arg Val Arg Val
            100                 105                 110

Pro Arg Arg Pro Gly Thr Leu Asp Gly Ser Glu Ala Gly Gly His Val
            115                 120                 125

Ser Ser Phe Val Pro Ala Cys Ser Leu Val Glu Ser His Leu Ser Asp
            130                 135                 140

Gln Leu Thr Leu His Val Asp Val Ala Gly Asn Val Val Gly Leu Ser
145                 150                 155                 160

Val Val Val Tyr Pro Gly Gly Cys Arg Gly Ser Glu Val Glu Asp Glu
                165                 170                 175

Asp Leu Glu Leu Phe Asn Thr Ser Val Gln Leu Arg Pro Ser Thr
            180                 185                 190

Ala Pro Gly Pro Glu Thr Ala Ala Phe Ile Glu Arg Leu Glu Met Glu
            195                 200                 205
```

```
Gln Ala Gln Lys Ala Lys Asn Pro Gln Glu Gln Lys Ser Phe Phe Ala
    210                 215                 220

Lys Tyr Trp Met Tyr Ile Ile Pro Val Val Leu Phe Leu Met Met Ser
225                 230                 235                 240

Gly Ala Pro Asp Ala Gly Gly Gln Gly Gly Gly Gly Gly Gly Gly Ser
                245                 250                 255

Ser Arg

<210> SEQ ID NO 6
<211> LENGTH: 254
<212> TYPE: PRT
<213> ORGANISM: Homo sapiens

<400> SEQUENCE: 6

Met Ala Ala Ala Ser Ala Gly Ala Thr Arg Leu Leu Leu Leu Leu Leu
1               5                   10                  15

Met Ala Val Ala Ala Pro Ser Arg Ala Arg Gly Ser Gly Cys Arg Ala
                20                  25                  30

Gly Thr Gly Ala Arg Gly Ala Gly Ala Glu Gly Arg Glu Gly Glu Ala
                35                  40                  45

Cys Gly Thr Val Gly Leu Leu Leu Glu His Ser Glu Ile Asp Asp
    50                  55                  60

Ser Ala Asn Phe Arg Lys Arg Gly Ser Leu Leu Trp Asn Gln Gln Asp
65                  70                  75                  80

Gly Thr Leu Ser Leu Ser Gln Arg Gln Leu Ser Glu Glu Glu Arg Gly
                85                  90                  95

Arg Leu Arg Asp Val Ala Ala Leu Asn Gly Leu Tyr Arg Val Arg Ile
                100                 105                 110

Pro Arg Arg Pro Gly Ala Leu Asp Gly Leu Glu Ala Gly Gly Tyr Val
                115                 120                 125

Ser Ser Phe Val Pro Ala Cys Ser Leu Val Glu Ser His Leu Ser Asp
        130                 135                 140

Gln Leu Thr Leu His Val Asp Val Ala Gly Asn Val Val Gly Val Ser
145                 150                 155                 160

Val Val Thr His Pro Gly Gly Cys Arg Gly His Glu Val Glu Asp Val
                165                 170                 175

Asp Leu Glu Leu Phe Asn Thr Ser Val Gln Leu Gln Pro Pro Thr Thr
                180                 185                 190

Ala Pro Gly Pro Glu Thr Ala Ala Phe Ile Glu Arg Leu Glu Met Glu
                195                 200                 205

Gln Ala Gln Lys Ala Lys Asn Pro Gln Glu Gln Lys Ser Phe Phe Ala
    210                 215                 220

Lys Tyr Trp His Ile Ile Leu Gly Gly Ala Val Leu Leu Thr Ala Leu
225                 230                 235                 240

Arg Pro Ala Thr Pro Gly Pro Ala Pro Pro Gln Glu Ala
                245                 250

<210> SEQ ID NO 7
<211> LENGTH: 254
<212> TYPE: PRT
<213> ORGANISM: Mus musculus

<400> SEQUENCE: 7

Met Val Ala Ala Gly Ala Gly Val Thr Arg Leu Leu Val Leu Leu Leu
1               5                   10                  15

Met Val Ala Ala Ala Pro Ser Arg Ala Arg Gly Ser Gly Cys Arg Val
                20                  25                  30
```

```
Gly Ala Ser Ala Arg Gly Thr Gly Ala Asp Gly Arg Glu Ala Glu Gly
            35                  40                  45

Cys Gly Thr Val Ala Leu Leu Leu Glu His Ser Phe Glu Leu Gly Asp
        50                  55                  60

Gly Ala Asn Phe Gln Lys Arg Gly Leu Leu Leu Trp Asn Gln Gln Asp
 65                  70                  75                  80

Gly Thr Leu Ser Ala Thr Gln Arg Gln Leu Ser Glu Glu Glu Arg Gly
                85                  90                  95

Arg Leu Arg Asp Val Ala Ala Val Asn Gly Leu Tyr Arg Val Arg Val
            100                 105                 110

Pro Arg Arg Pro Gly Thr Leu Asp Gly Ser Glu Ala Gly Gly His Val
            115                 120                 125

Ser Ser Phe Val Pro Ala Cys Ser Leu Val Glu Ser His Leu Ser Asp
            130                 135                 140

Gln Leu Thr Leu His Val Asp Val Ala Gly Asn Val Val Gly Leu Ser
145                 150                 155                 160

Val Val Val Tyr Pro Gly Gly Cys Arg Gly Ser Glu Val Glu Asp Glu
                165                 170                 175

Asp Leu Glu Leu Phe Asn Thr Ser Val Gln Leu Arg Pro Pro Ser Thr
            180                 185                 190

Ala Pro Gly Pro Glu Thr Ala Ala Phe Ile Glu Arg Leu Glu Met Glu
            195                 200                 205

Gln Ala Gln Lys Ala Lys Asn Pro Gln Glu Gln Lys Ser Phe Phe Ala
            210                 215                 220

Lys Tyr Trp His Leu Ile Leu Gly Gly Ala Val Leu Leu Thr Ala Leu
225                 230                 235                 240

Arg Pro Ala Ala Pro Gly Pro Ala Pro Ala Pro Thr Glu Ala
                245                 250

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 8

His His His His His His
1               5
```